US008314291B2

(12) United States Patent
Ono et al.

(10) Patent No.: US 8,314,291 B2
(45) Date of Patent: Nov. 20, 2012

(54) METHOD FOR PRODUCING PLANT WITH MODIFIED FLOWER MORPHOLOGY

(75) Inventors: Michiyuki Ono, Tsukuba (JP); Teruhiko Terakawa, Atsugi (JP); Masaru Takagi, Tsukuba (JP)

(73) Assignees: University of Tsukuba, Tsukuba-shi, Ibaraki (JP); National Institute of Advanced Industrial Science and Technology, Chiyoda-ku, Tokyo (JP); Hokko Chemical Industry Co., Ltd., Chuo-ku, Tokyo (JP)

( * ) Notice: Subject to any disclaimer, the term of this patent is extended or adjusted under 35 U.S.C. 154(b) by 261 days.

(21) Appl. No.: 12/672,489

(22) PCT Filed: Aug. 4, 2008

(86) PCT No.: PCT/JP2008/063973
§ 371 (c)(1),
(2), (4) Date: Feb. 5, 2010

(87) PCT Pub. No.: WO2009/020101
PCT Pub. Date: Feb. 12, 2009

(65) Prior Publication Data
US 2010/0146666 A1 Jun. 10, 2010

(30) Foreign Application Priority Data
Aug. 6, 2007 (JP) ................................ 2007-204253

(51) Int. Cl.
*C12N 15/82* (2006.01)
*A01H 5/00* (2006.01)
(52) U.S. Cl. .................. 800/278; 800/290; 800/298
(58) Field of Classification Search ........................ None
See application file for complete search history.

(56) References Cited

U.S. PATENT DOCUMENTS

| 7,342,148 B2 | 3/2008 | Takagi |
| 2005/0183169 A1 | 8/2005 | Takagi et al. |

FOREIGN PATENT DOCUMENTS

| EP | 1702508 | 9/2006 |
| JP | 11-318462 | 11/1999 |
| JP | 2001-269176 | 10/2001 |
| JP | 2001-269177 | 10/2001 |
| JP | 2001-269178 | 10/2001 |
| JP | 2001-269179 | 10/2001 |
| JP | 2001-292776 | 10/2001 |
| JP | 2001-292777 | 10/2001 |
| JP | 2005-192483 | 7/2005 |
| JP | 2005-295879 | 10/2005 |
| JP | 2006-42729 | 2/2006 |
| WO | WO 03/054007 | 7/2003 |

OTHER PUBLICATIONS

Jang et al (2004, Plant Molecular Biology 56:133-143).*
Hiratsu et al (2003, The Plant Journal 34:733-739).*
Siegfried et al (1999, Development 126:4117-4128.*
Bowie et al, Science 247:1306-1310, 1990, see especially p. 1306.*
McConnell et al, Nature 411 (6838):709-713, 2001.*
Alvarez, et al. "Endogenous and Synthetic MicroRNAs Stimulate Simultaneous, Efficient, and Localized Regulation of multiple Targets in Diverse Species," *The Plant Cell*, vol. 18, pp. 1134-1151, May 2006.
Dai, et al. "A Wuschel-Like Homeobox Gene Represses a YABBY Gene Expression required for Rice Leaf Development," *Plant Physiol.*, vol. 144, pp. 380-390, May 2007.
Iwasaki, et al. "The Feathered Gene is Required for Polarity Establishment in Lateral Organs Especially Flowers of the Japanese Morning Glory (*Ipomoea nil*)," *Plant Mol. Biol.*, vol. 62, pp. 913-925, 2006.
Hiyama, et al. "CRES-T Ho ni yoru Hanagata Kaihen -Henka Asagao ni Semaru," BMB2007 (Dai 30 Kai Annual Meeting of the Molecular Biology Society of Japan, Dai 80 Kai Nenkai) Koen Yoshishu, Nov. 25, 2007, p. 537 (abstract 2P-1421).
International Search Report dated Sep. 9, 2008 and issued to the corresponding international application PCT/JP2008/063973.
Kumaran, et al. "Molecular Cloning of Abnormal Floral Organs: A Gene Required for Flower Development in *Arabidopsis*," *Sexual Plant Reproduction*, vol. 12, No. 2, pp. 118-122, Jun. 1999.
Siegfried, et al. "Members of the *YABBY* Gene Family Specify Abaxial Cell Fate in *Arabidopsis*," *Development*, vol. 126, No. 18, pp. 4117-4128, Sep. 1999.
Supplementary European Search Report mailed Aug. 4, 2010, issued to European patent application EP 08 79 2170.
Office Action dated Aug. 25, 2011 issued to corresponding European patent application No. 08 792 170.6.
Hiyama, et al. "CRES-T Ho ni yoru Hanagata Kaihen -Henka Asagao ni Semaru-," BMB2007 (Dai 30 Kai Annual Meeting of the Molecular Biology Society of Japan, Dai 80 Kai The Japanese Biochemical Society Taikai Godo Nenkai) Koen Yoshishu, Nov. 25, 2007, p. 537 (abstract 2P-1421).
Eshed, et al. "Establishment of Polarity in Lateral Organs of Plants," *Current Biology*, vol. 11, pp. 1251-1260, 2001.
Eshed, et al. "Asymmetric Leaf Development and Blade Expansion in *Arabidopsis* are Mediated by KANADI and YABBY Activities," *Development*, vol. 131, pp. 2997-3006, 2004.
Kidner, "Mixing and Matching Pathways in Leaf Polarity," *Current Opinion in Plant Biology*, vol. 10, pp. 13-20, 2007.
Robert J. Meister et al., "Multiple Protein Regions Contribute to Differential Activities of YABBY Proteins in Reproductive Development $^{1[W][}$", Plant Physiology, Feb. 2005, vol. 137, pp. 651-662, www.plantphysiol.org, American Society of Plant Biologists.

* cited by examiner

*Primary Examiner* — Stuart F. Baum
(74) *Attorney, Agent, or Firm* — Knobbe, Martens, Olson & Bear, LLP

(57) ABSTRACT

A plant with modified flower morphology is produced by suppressing a function of a transcription factor involved in determining the polarity of plants. More particularly, a plant with modified flower morphology is produced by the steps of obtaining a transformed cell by introducing a chimeric DNA in which a DNA encoding a transcription factor involved in determining the polarity and a functional peptide converting a transcription factor into a transcription repressor are fused; and regenerating a transformed plant from the transformed cell.

6 Claims, 1 Drawing Sheet

(a) Wild type  (b) Transformed type (a) Wild type  (b) Transformed type (a) Wild type  (b) Transformed type

SEQUENCE LISTING

```
<160> NUMBER OF SEQ ID NOS: 60

<210> SEQ ID NO 1
<211> LENGTH: 1212
<212> TYPE: DNA
<213> ORGANISM: Arabidopsis thaliana
<220> FEATURE:
<221> NAME/KEY: CDS
<222> LOCATION: (1)..(1209)

<400> SEQUENCE: 1 atg tct atg gaa ggt gtt ttt cta gag aaa acc aaa aca aac aca aca         48
Met Ser Met Glu Gly Val Phe Leu Glu Lys Thr Lys Thr Asn Thr Thr
1               5                   10                  15 act act ctc cct gat cta tct ctc cac atc agt ctc cca gat att cat         96
Thr Thr Leu Pro Asp Leu Ser Leu His Ile Ser Leu Pro Asp Ile His
                20                  25                  30 caa tac cat cac aat gaa tct tct aaa gaa tct tca aga aga tcc tcc        144
Gln Tyr His His Asn Glu Ser Ser Lys Glu Ser Ser Arg Arg Ser Ser
            35                  40                  45 caa ctc gaa aac aac aac cga tcg tcc aac ttt gaa ctc tct tta tct        192
Gln Leu Glu Asn Asn Asn Arg Ser Ser Asn Phe Glu Leu Ser Leu Ser
        50                  55                  60 cat cat aac cat cca aca gca aga atc ttc cat tgt cct gat cga aga        240
His His Asn His Pro Thr Ala Arg Ile Phe His Cys Pro Asp Arg Arg
65                  70                  75                  80 acc ctt aat ctt cct cat cag cag cat tac aac aac cct atc atc aat        288
Thr Leu Asn Leu Pro His Gln Gln His Tyr Asn Asn Pro Ile Ile Asn
                85                  90                  95 ggt gtt cat caa agg gtc gat gaa tcc gag att agt aat ctc cac cgt        336
Gly Val His Gln Arg Val Asp Glu Ser Glu Ile Ser Asn Leu His Arg
            100                 105                 110 cca att aga ggc atc ccg gtc tat cac aac cgt tca ttc cct ttc cac        384
Pro Ile Arg Gly Ile Pro Val Tyr His Asn Arg Ser Phe Pro Phe His
        115                 120                 125 caa caa aac tct tca tta cct tct ctt gga gga gga gac atg gat caa        432
Gln Gln Asn Ser Ser Leu Pro Ser Leu Gly Gly Gly Asp Met Asp Gln
    130                 135                 140 atc tca atc tta aac tca tct tcc ggc tac aac aac gct tac cga tca        480
Ile Ser Ile Leu Asn Ser Ser Ser Gly Tyr Asn Asn Ala Tyr Arg Ser
145                 150                 155                 160 tta caa tct tcc ccg agg ctt aaa ggt gtt cct ttg cat cat cat cat        528
Leu Gln Ser Ser Pro Arg Leu Lys Gly Val Pro Leu His His His His
                165                 170                 175
```

|  |  |
|---|---|
| cat cat aat cag tat gga gtc gtt gga tct tca gat tcg tct tct cct<br>His His Asn Gln Tyr Gly Val Val Gly Ser Ser Asp Ser Ser Ser Pro<br>           180                        185                 190 | 576 |
| cat cac cat aac cat cat cat cat ggg atg atc aga tca aga ttc ttg<br>His His His Asn His His His His Gly Met Ile Arg Ser Arg Phe Leu<br>           195                        200                 205 | 624 |
| cct aag atg ccg aca aag cga agc atg aga gct cca agg atg cgt tgg<br>Pro Lys Met Pro Thr Lys Arg Ser Met Arg Ala Pro Arg Met Arg Trp<br>           210                        215                 220 | 672 |
| act agt agc ctc cac gcg cgg ttt gtt cac gct gtt gag ctt cta ggc<br>Thr Ser Ser Leu His Ala Arg Phe Val His Ala Val Glu Leu Leu Gly<br>225                     230                        235                 240 | 720 |
| ggc cat gaa aga gca act cca aag tcg gtt ctt gag ctc atg gat gta<br>Gly His Glu Arg Ala Thr Pro Lys Ser Val Leu Glu Leu Met Asp Val<br>                     245                        250                 255 | 768 |
| aaa gac tta act tta gca cat gtg aag agc cat ttg cag atg tat cga<br>Lys Asp Leu Thr Leu Ala His Val Lys Ser His Leu Gln Met Tyr Arg<br>           260                        265                 270 | 816 |
| act gtt aag acc act aac aag cct gct gct tca tca gat ggg tca gga<br>Thr Val Lys Thr Thr Asn Lys Pro Ala Ala Ser Ser Asp Gly Ser Gly<br>                275                        280                 285 | 864 |
| gaa gaa gaa atg ggc ata aat gga aac gaa gtt cat cat caa tca tcg<br>Glu Glu Glu Met Gly Ile Asn Gly Asn Glu Val His His Gln Ser Ser<br>           290                        295                 300 | 912 |
| acg gat caa agg gca caa tct gat gat act tct ctt cat caa gaa act<br>Thr Asp Gln Arg Ala Gln Ser Asp Asp Thr Ser Leu His Gln Glu Thr<br>305                     310                        315                 320 | 960 |
| gac att tct tcc aca caa cct cgt tgg agt aac tct tca cga gag aca<br>Asp Ile Ser Ser Thr Gln Pro Arg Trp Ser Asn Ser Ser Arg Glu Thr<br>                325                        330                 335 | 1008 |
| tgg cca tta agt aat aac tgc tca agc gac ata gat aca atg atc aga<br>Trp Pro Leu Ser Asn Asn Cys Ser Ser Asp Ile Asp Thr Met Ile Arg<br>                   340                       345                 350 | 1056 |
| act tca tca aca tca atg atc tct cat tat caa aga tcc agc att caa<br>Thr Ser Ser Thr Ser Met Ile Ser His Tyr Gln Arg Ser Ser Ile Gln<br>                355                        360                 365 | 1104 |
| aat cag gag caa agg tcg aat gat caa gca aag agg tgt gga aat ctt<br>Asn Gln Glu Gln Arg Ser Asn Asp Gln Ala Lys Arg Cys Gly Asn Leu<br>           370                        375                 380 | 1152 |
| agt tgt gaa aat cca agt ttg gag ttt aca tta ggc aga cca gat tgg<br>Ser Cys Glu Asn Pro Ser Leu Glu Phe Thr Leu Gly Arg Pro Asp Trp<br>385                     390                        395                 400 | 1200 |
| cac gag aaa tga<br>His Glu Lys | 1212 |

```
<210> SEQ ID NO 2
<211> LENGTH: 403
<212> TYPE: PRT
<213> ORGANISM: Arabidopsis thaliana

<400> SEQUENCE: 2
```

Met Ser Met Glu Gly Val Phe Leu Glu Lys Thr Lys Thr Asn Thr Thr
1                 5                    10                 15

Thr Thr Leu Pro Asp Leu Ser Leu His Ile Ser Leu Pro Asp Ile His
           20                       25                    30

Gln Tyr His His Asn Glu Ser Ser Lys Glu Ser Ser Arg Arg Ser Ser
              35                       40                    45

Gln Leu Glu Asn Asn Asn Arg Ser Ser Asn Phe Glu Leu Ser Leu Ser
 50                    55                       60

His His Asn His Pro Thr Ala Arg Ile Phe His Cys Pro Asp Arg Arg
 65                  70                  75                  80

Thr Leu Asn Leu Pro His Gln Gln His Tyr Asn Asn Pro Ile Ile Asn
             85                  90                  95

Gly Val His Gln Arg Val Asp Glu Ser Glu Ile Ser Asn Leu His Arg
            100                 105                 110

Pro Ile Arg Gly Ile Pro Val Tyr His Asn Arg Ser Phe Pro Phe His
        115                 120                 125

Gln Gln Asn Ser Ser Leu Pro Ser Leu Gly Gly Asp Met Asp Gln
130                 135                 140

Ile Ser Ile Leu Asn Ser Ser Gly Tyr Asn Asn Ala Tyr Arg Ser
145                 150                 155                 160

Leu Gln Ser Ser Pro Arg Leu Lys Gly Val Pro Leu His His His
                165                 170                 175

His His Asn Gln Tyr Gly Val Val Gly Ser Ser Asp Ser Ser Ser Pro
            180                 185                 190

His His His Asn His His His Gly Met Ile Arg Ser Arg Phe Leu
        195                 200                 205

Pro Lys Met Pro Thr Lys Arg Ser Met Arg Ala Pro Arg Met Arg Trp
210                 215                 220

Thr Ser Ser Leu His Ala Arg Phe Val His Ala Val Glu Leu Leu Gly
225                 230                 235                 240

Gly His Glu Arg Ala Thr Pro Lys Ser Val Leu Glu Leu Met Asp Val
                245                 250                 255

Lys Asp Leu Thr Leu Ala His Val Lys Ser His Leu Gln Met Tyr Arg
            260                 265                 270

Thr Val Lys Thr Thr Asn Lys Pro Ala Ala Ser Ser Asp Gly Ser Gly
        275                 280                 285

Glu Glu Glu Met Gly Ile Asn Gly Asn Glu Val His His Gln Ser Ser
290                 295                 300

Thr Asp Gln Arg Ala Gln Ser Asp Asp Thr Ser Leu His Gln Glu Thr
305                 310                 315                 320

Asp Ile Ser Ser Thr Gln Pro Arg Trp Ser Asn Ser Ser Arg Glu Thr
                325                 330                 335

Trp Pro Leu Ser Asn Asn Cys Ser Ser Asp Ile Asp Thr Met Ile Arg
            340                 345                 350

Thr Ser Ser Thr Ser Met Ile Ser His Tyr Gln Arg Ser Ser Ile Gln
        355                 360                 365

Asn Gln Glu Gln Arg Ser Asn Asp Gln Ala Lys Arg Cys Gly Asn Leu
370                 375                 380

Ser Cys Glu Asn Pro Ser Leu Glu Phe Thr Leu Gly Arg Pro Asp Trp
385                 390                 395                 400

His Glu Lys

<210> SEQ ID NO 3
<211> LENGTH: 690
<212> TYPE: DNA
<213> ORGANISM: Arabidopsis thaliana
<220> FEATURE:
<221> NAME/KEY: CDS
<222> LOCATION: (1)..(687)

<400> SEQUENCE: 3 atg tct atg tcg tct atg tcc tcc cct tcc tca gct gtt tgt tca ccg    48
Met Ser Met Ser Ser Met Ser Ser Pro Ser Ser Ala Val Cys Ser Pro
1               5                   10                  15

```
gac cac ttc tct cct tcc gac cat ctc tgc tat gtc caa tgc aac ttt    96
Asp His Phe Ser Pro Ser Asp His Leu Cys Tyr Val Gln Cys Asn Phe
             20                  25                  30 tgc caa acc atc ctt gcg gtt aat gtt cct tac aca agc ttg ttc aag   144
Cys Gln Thr Ile Leu Ala Val Asn Val Pro Tyr Thr Ser Leu Phe Lys
         35                  40                  45 acc gta act gtc cga tgt ggt tgc tgt acc aat ctc ctt tcg gtg aac   192
Thr Val Thr Val Arg Cys Gly Cys Cys Thr Asn Leu Leu Ser Val Asn
 50                  55                  60 atg aga tca tat gtc ctc cca gct tct aac cag ctc cag ctc cag ctc   240
Met Arg Ser Tyr Val Leu Pro Ala Ser Asn Gln Leu Gln Leu Gln Leu
 65                  70                  75                  80 ggt cct cac tct tac ttc aat ccc cag gat att ctg gag gag ctg aga   288
Gly Pro His Ser Tyr Phe Asn Pro Gln Asp Ile Leu Glu Glu Leu Arg
                 85                  90                  95 gat gca ccg tct aac atg aat atg atg atg atg aat caa cat cct act   336
Asp Ala Pro Ser Asn Met Asn Met Met Met Met Asn Gln His Pro Thr
            100                 105                 110 atg aat gac ata cca tct ttc atg gat ctt cat caa caa cat gag att   384
Met Asn Asp Ile Pro Ser Phe Met Asp Leu His Gln Gln His Glu Ile
        115                 120                 125 cct aaa gca cca ccc gtt aac cgc cct cca gag aaa aga cag aga gtc   432
Pro Lys Ala Pro Pro Val Asn Arg Pro Pro Glu Lys Arg Gln Arg Val
    130                 135                 140 cca tcc gca tat aac cga ttc atc aag gag gag atc caa cgt atc aaa   480
Pro Ser Ala Tyr Asn Arg Phe Ile Lys Glu Glu Ile Gln Arg Ile Lys
145                 150                 155                 160 gct ggt aat cct gat ata agc cac aga gaa gcc ttt agt gct gct gcc   528
Ala Gly Asn Pro Asp Ile Ser His Arg Glu Ala Phe Ser Ala Ala Ala
                165                 170                 175 aag aat tgg gcc cac ttc ccc cac ata cac ttc ggg ctc gtg cca gac   576
Lys Asn Trp Ala His Phe Pro His Ile His Phe Gly Leu Val Pro Asp
            180                 185                 190 aat caa ccc gtg aag aaa acc aac atg ccc caa cag gag gga gag gat   624
Asn Gln Pro Val Lys Lys Thr Asn Met Pro Gln Gln Glu Gly Glu Asp
        195                 200                 205 aac atg gtg atg aaa gaa ggg ttc tac gct cct gca gct gct aac gtt   672
Asn Met Val Met Lys Glu Gly Phe Tyr Ala Pro Ala Ala Ala Asn Val
    210                 215                 220 ggt gtg act cct tat taa                                            690
Gly Val Thr Pro Tyr
225
```

<210> SEQ ID NO 4
<211> LENGTH: 229
<212> TYPE: PRT
<213> ORGANISM: Arabidopsis thaliana

<400> SEQUENCE: 4

```
Met Ser Met Ser Ser Met Ser Ser Pro Ser Ser Ala Val Cys Ser Pro
 1               5                  10                  15

Asp His Phe Ser Pro Ser Asp His Leu Cys Tyr Val Gln Cys Asn Phe
             20                  25                  30

Cys Gln Thr Ile Leu Ala Val Asn Val Pro Tyr Thr Ser Leu Phe Lys
         35                  40                  45

Thr Val Thr Val Arg Cys Gly Cys Cys Thr Asn Leu Leu Ser Val Asn
 50                  55                  60

Met Arg Ser Tyr Val Leu Pro Ala Ser Asn Gln Leu Gln Leu Gln Leu
 65                  70                  75                  80
```

-continued

```
Gly Pro His Ser Tyr Phe Asn Pro Gln Asp Ile Leu Glu Glu Leu Arg
                 85                  90                  95

Asp Ala Pro Ser Asn Met Asn Met Met Met Asn Gln His Pro Thr
            100                 105                 110

Met Asn Asp Ile Pro Ser Phe Met Asp Leu His Gln Gln His Glu Ile
        115                 120                 125

Pro Lys Ala Pro Pro Val Asn Arg Pro Pro Glu Lys Arg Gln Arg Val
    130                 135                 140

Pro Ser Ala Tyr Asn Arg Phe Ile Lys Glu Glu Ile Gln Arg Ile Lys
145                 150                 155                 160

Ala Gly Asn Pro Asp Ile Ser His Arg Glu Ala Phe Ser Ala Ala Ala
                165                 170                 175

Lys Asn Trp Ala His Phe Pro His Ile His Phe Gly Leu Val Pro Asp
            180                 185                 190

Asn Gln Pro Val Lys Lys Thr Asn Met Pro Gln Gln Glu Gly Glu Asp
        195                 200                 205

Asn Met Val Met Lys Glu Gly Phe Tyr Ala Pro Ala Ala Asn Val
    210                 215                 220

Gly Val Thr Pro Tyr
225
```

<210> SEQ ID NO 5
<211> LENGTH: 2559
<212> TYPE: DNA
<213> ORGANISM: Arabidopsis thaliana
<220> FEATURE:
<221> NAME/KEY: CDS
<222> LOCATION: (1)..(2556)

<400> SEQUENCE: 5

```
atg atg atg gtc cat tcg atg agc aga gat atg atg aac aga gag tcg      48
Met Met Met Val His Ser Met Ser Arg Asp Met Met Asn Arg Glu Ser
1               5                   10                  15 ccg gat aaa ggg tta gat tcc ggc aag tat gtg agg tac acg ccg gag      96
Pro Asp Lys Gly Leu Asp Ser Gly Lys Tyr Val Arg Tyr Thr Pro Glu
            20                  25                  30 caa gtg gaa gct ctc gag aga gtt tac act gag tgt cct aag cca agt     144
Gln Val Glu Ala Leu Glu Arg Val Tyr Thr Glu Cys Pro Lys Pro Ser
        35                  40                  45 tct cta aga aga caa caa ctc ata cgt gaa tgt ccg att ctc tct aac     192
Ser Leu Arg Arg Gln Gln Leu Ile Arg Glu Cys Pro Ile Leu Ser Asn
    50                  55                  60 atc gag cct aag cag atc aaa gtt tgg ttt cag aac cgc aga tgt cgt     240
Ile Glu Pro Lys Gln Ile Lys Val Trp Phe Gln Asn Arg Arg Cys Arg
65                  70                  75                  80 gag aag cag agg aaa gaa gct gct cgt ctt caa aca gtg aac aga aaa     288
Glu Lys Gln Arg Lys Glu Ala Ala Arg Leu Gln Thr Val Asn Arg Lys
                85                  90                  95 ctc aat gcc atg aac aaa ctc ttg atg gaa gag aat gat cgt ttg cag     336
Leu Asn Ala Met Asn Lys Leu Leu Met Glu Glu Asn Asp Arg Leu Gln
            100                 105                 110 aag caa gtt tct aac ttg gtc tat gag aat ggc cac atg aaa cat caa     384
Lys Gln Val Ser Asn Leu Val Tyr Glu Asn Gly His Met Lys His Gln
        115                 120                 125 ctt cac act gct tct ggg acg acc aca gac aac agc tgt gag tct gtg     432
Leu His Thr Ala Ser Gly Thr Thr Thr Asp Asn Ser Cys Glu Ser Val
    130                 135                 140 gtc gtg agt ggt cag caa cat caa cag caa aac cca aat cct cag cat     480
Val Val Ser Gly Gln Gln His Gln Gln Gln Asn Pro Asn Pro Gln His
145                 150                 155                 160
```

```
                                                -continued cag caa cgt gat gct aac aac cca gca gga ctc ctt tct ata gca gag       528
Gln Gln Arg Asp Ala Asn Asn Pro Ala Gly Leu Leu Ser Ile Ala Glu
            165                 170                 175 gag gcc cta gca gag ttc ctt tcc aag gct aca gga act gct gtt gac       576
Glu Ala Leu Ala Glu Phe Leu Ser Lys Ala Thr Gly Thr Ala Val Asp
        180                 185                 190 tgg gtt cag atg att ggg atg aag cct ggt ccg gat tct att ggc ata       624
Trp Val Gln Met Ile Gly Met Lys Pro Gly Pro Asp Ser Ile Gly Ile
    195                 200                 205 gtc gct att tcg cgc aac tgc agc gga att gca gca cgt gcc tgc ggc       672
Val Ala Ile Ser Arg Asn Cys Ser Gly Ile Ala Ala Arg Ala Cys Gly
210                 215                 220 ctc gtg agt tta gaa ccc atg aag gtt gct gaa att ctc aaa gat cgt       720
Leu Val Ser Leu Glu Pro Met Lys Val Ala Glu Ile Leu Lys Asp Arg
225                 230                 235                 240 cca tct tgg ctc cga gat tgt cga agt gtg gat act ctg agt gtg ata       768
Pro Ser Trp Leu Arg Asp Cys Arg Ser Val Asp Thr Leu Ser Val Ile
                245                 250                 255 cct gct gga aac ggt ggg acg atc gag ctt att tac acg cag atg tat       816
Pro Ala Gly Asn Gly Gly Thr Ile Glu Leu Ile Tyr Thr Gln Met Tyr
            260                 265                 270 gct cct acg act tta gca gca gct cgt gac ttt tgg acg ctg aga tat       864
Ala Pro Thr Thr Leu Ala Ala Ala Arg Asp Phe Trp Thr Leu Arg Tyr
        275                 280                 285 agc aca tgt ttg gaa gat gga agc tat gtg gtt tgt gaa agg tcg ctt       912
Ser Thr Cys Leu Glu Asp Gly Ser Tyr Val Val Cys Glu Arg Ser Leu
    290                 295                 300 act tct gca act ggt ggc ccc act ggg cca cct tct tca aac ttt gtg       960
Thr Ser Ala Thr Gly Gly Pro Thr Gly Pro Pro Ser Ser Asn Phe Val
305                 310                 315                 320 aga gct gaa atg aaa cca agc ggg ttt ctc atc cgt cct tgc gat ggt      1008
Arg Ala Glu Met Lys Pro Ser Gly Phe Leu Ile Arg Pro Cys Asp Gly
                325                 330                 335 ggt ggt tcc att ctc cac att gtt gat cat gtt gat ctg gat gcc tgg      1056
Gly Gly Ser Ile Leu His Ile Val Asp His Val Asp Leu Asp Ala Trp
            340                 345                 350 agt gtc cct gaa gtc atg agg cct ctc tat gaa tca tcg aag att ctt      1104
Ser Val Pro Glu Val Met Arg Pro Leu Tyr Glu Ser Ser Lys Ile Leu
        355                 360                 365 gct cag aaa atg act gtt gct gct ttg aga cat gta aga caa att gca      1152
Ala Gln Lys Met Thr Val Ala Ala Leu Arg His Val Arg Gln Ile Ala
    370                 375                 380 caa gaa aca agt gga gaa gtt cag tat ggt gga ggg cgc caa cct gcg      1200
Gln Glu Thr Ser Gly Glu Val Gln Tyr Gly Gly Gly Arg Gln Pro Ala
385                 390                 395                 400 gtt tta aga acc ttc agt caa aga ctc tgt cgg ggt ttc aat gat gct      1248
Val Leu Arg Thr Phe Ser Gln Arg Leu Cys Arg Gly Phe Asn Asp Ala
                405                 410                 415 gtt aat ggt ttt gtg gat gat gga tgg tca cca atg ggt agc gat ggt      1296
Val Asn Gly Phe Val Asp Asp Gly Trp Ser Pro Met Gly Ser Asp Gly
            420                 425                 430 gca gag gat gtt act gta atg ata aac ttg tcc cct ggg aag ttt ggt      1344
Ala Glu Asp Val Thr Val Met Ile Asn Leu Ser Pro Gly Lys Phe Gly
        435                 440                 445 ggg tct cag tac ggt aat tca ttc ctt cca agc ttt ggt agt ggc gtg      1392
Gly Ser Gln Tyr Gly Asn Ser Phe Leu Pro Ser Phe Gly Ser Gly Val
    450                 455                 460 ctt tgt gcc aag gca tct atg ttg ctt cag aac gtt cca ccc gct gtg      1440
Leu Cys Ala Lys Ala Ser Met Leu Leu Gln Asn Val Pro Pro Ala Val
465                 470                 475                 480
```

```
ctg gtt cga ttc ctt aga gaa cac cga tct gaa tgg gct gat tat ggc      1488
Leu Val Arg Phe Leu Arg Glu His Arg Ser Glu Trp Ala Asp Tyr Gly
            485                 490                 495 gtg gat gct tat gct gct gca tcg ctc aga gca agt cct ttt gct gtt      1536
Val Asp Ala Tyr Ala Ala Ala Ser Leu Arg Ala Ser Pro Phe Ala Val
        500                 505                 510 cct tgt gct aga gct ggg ggg ttc cca agt aac caa gtc att ctt cct      1584
Pro Cys Ala Arg Ala Gly Gly Phe Pro Ser Asn Gln Val Ile Leu Pro
    515                 520                 525 ctt gcg cag aca gtt gaa cat gaa gag tca ctt gag gtg gtt aga ctt      1632
Leu Ala Gln Thr Val Glu His Glu Glu Ser Leu Glu Val Val Arg Leu
530                 535                 540 gaa ggt cac gct tac tca ccc gaa gac atg ggt tta gct cgg gat atg      1680
Glu Gly His Ala Tyr Ser Pro Glu Asp Met Gly Leu Ala Arg Asp Met
545                 550                 555                 560 tat ttg cta cag ctt tgt agc ggt gtt gat gaa aat gtg gtt gga ggt      1728
Tyr Leu Leu Gln Leu Cys Ser Gly Val Asp Glu Asn Val Val Gly Gly
                565                 570                 575 tgt gca cag ctt gta ttt gcc cct atc gat gaa tca ttt gct gat gat      1776
Cys Ala Gln Leu Val Phe Ala Pro Ile Asp Glu Ser Phe Ala Asp Asp
            580                 585                 590 gca cct ttg ctt cct tcc ggt ttc cgc atc ata cct ctt gaa cag aaa      1824
Ala Pro Leu Leu Pro Ser Gly Phe Arg Ile Ile Pro Leu Glu Gln Lys
        595                 600                 605 tct act ccg aac ggt gca tct gca aac cgt acc ctg gat tta gcc tca      1872
Ser Thr Pro Asn Gly Ala Ser Ala Asn Arg Thr Leu Asp Leu Ala Ser
    610                 615                 620 gct tta gaa gga tcc aca cgt caa gct ggt gaa gcc gac cca aat ggc      1920
Ala Leu Glu Gly Ser Thr Arg Gln Ala Gly Glu Ala Asp Pro Asn Gly
625                 630                 635                 640 tgt aac ttt agg tcg gta cta acc ata gca ttc cag ttc aca ttt gat      1968
Cys Asn Phe Arg Ser Val Leu Thr Ile Ala Phe Gln Phe Thr Phe Asp
                645                 650                 655 aac cat tca aga gac agt gtt gct tca atg gca cgt cag tac gtg cga      2016
Asn His Ser Arg Asp Ser Val Ala Ser Met Ala Arg Gln Tyr Val Arg
            660                 665                 670 agc ata gta gga tcg att cag agg gtt gct cta gcc att gct cct cgt      2064
Ser Ile Val Gly Ser Ile Gln Arg Val Ala Leu Ala Ile Ala Pro Arg
        675                 680                 685 cct ggc tcc aat atc agt cca ata tct gtt ccc act tcc cct gaa gct      2112
Pro Gly Ser Asn Ile Ser Pro Ile Ser Val Pro Thr Ser Pro Glu Ala
    690                 695                 700 ctc act ctg gtc cgt tgg atc tcc cgg agt tac agc ctt cac act ggt      2160
Leu Thr Leu Val Arg Trp Ile Ser Arg Ser Tyr Ser Leu His Thr Gly
705                 710                 715                 720 gca gat ctc ttt gga tct gat tct caa acc agt ggt gac acg ttg ctg      2208
Ala Asp Leu Phe Gly Ser Asp Ser Gln Thr Ser Gly Asp Thr Leu Leu
                725                 730                 735 cat caa ctc tgg aat cac tct gat gca atc ttg tgc tgc tcc ctc aaa      2256
His Gln Leu Trp Asn His Ser Asp Ala Ile Leu Cys Cys Ser Leu Lys
            740                 745                 750 aca aac gct tca ccg gtt ttc aca ttc gca aac caa acc ggt tta gac      2304
Thr Asn Ala Ser Pro Val Phe Thr Phe Ala Asn Gln Thr Gly Leu Asp
        755                 760                 765 atg ctg gaa acg act ctt gta gcc ctt caa gac ata atg cta gac aag      2352
Met Leu Glu Thr Thr Leu Val Ala Leu Gln Asp Ile Met Leu Asp Lys
    770                 775                 780 acc ctt gac gaa cct ggt cgt aaa gct ctt tgc tct gag ttc ccc aag      2400
Thr Leu Asp Glu Pro Gly Arg Lys Ala Leu Cys Ser Glu Phe Pro Lys
785                 790                 795                 800
```

```
atc atg caa cag ggc tat gct cat ctg ccg gca gga gta tgt gcg tca    2448
Ile Met Gln Gln Gly Tyr Ala His Leu Pro Ala Gly Val Cys Ala Ser
            805                 810                 815 agc atg gga agg atg gta tct tac gag cag gca acg gtg tgg aaa gtt    2496
Ser Met Gly Arg Met Val Ser Tyr Glu Gln Ala Thr Val Trp Lys Val
            820                 825                 830 ctt gaa gac gat gaa tca aac cac tgc tta gct ttc atg ttc gtg aat    2544
Leu Glu Asp Asp Glu Ser Asn His Cys Leu Ala Phe Met Phe Val Asn
            835                 840                 845 tgg tcg ttc gtt tga                                                2559
Trp Ser Phe Val
    850

<210> SEQ ID NO 6
<211> LENGTH: 852
<212> TYPE: PRT
<213> ORGANISM: Arabidopsis thaliana

<400> SEQUENCE: 6

Met Met Met Val His Ser Met Ser Arg Asp Met Met Asn Arg Glu Ser
1               5                   10                  15

Pro Asp Lys Gly Leu Asp Ser Gly Lys Tyr Val Arg Tyr Thr Pro Glu
            20                  25                  30

Gln Val Glu Ala Leu Glu Arg Val Tyr Thr Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ala Ala Arg Leu Gln Thr Val Asn Arg Lys
                85                  90                  95

Leu Asn Ala Met Asn Lys Leu Leu Met Glu Glu Asn Asp Arg Leu Gln
            100                 105                 110

Lys Gln Val Ser Asn Leu Val Tyr Glu Asn Gly His Met Lys His Gln
        115                 120                 125

Leu His Thr Ala Ser Gly Thr Thr Thr Asp Asn Ser Cys Glu Ser Val
    130                 135                 140

Val Val Ser Gly Gln Gln His Gln Gln Gln Asn Pro Asn Pro Gln His
145                 150                 155                 160

Gln Gln Arg Asp Ala Asn Asn Pro Ala Gly Leu Leu Ser Ile Ala Glu
                165                 170                 175

Glu Ala Leu Ala Glu Phe Leu Ser Lys Ala Thr Gly Thr Ala Val Asp
            180                 185                 190

Trp Val Gln Met Ile Gly Met Lys Pro Gly Pro Asp Ser Ile Gly Ile
        195                 200                 205

Val Ala Ile Ser Arg Asn Cys Ser Gly Ile Ala Ala Arg Ala Cys Gly
    210                 215                 220

Leu Val Ser Leu Glu Pro Met Lys Val Ala Glu Ile Leu Lys Asp Arg
225                 230                 235                 240

Pro Ser Trp Leu Arg Asp Cys Arg Ser Val Asp Thr Leu Ser Val Ile
                245                 250                 255

Pro Ala Gly Asn Gly Gly Thr Ile Glu Leu Ile Tyr Thr Gln Met Tyr
            260                 265                 270

Ala Pro Thr Thr Leu Ala Ala Ala Arg Asp Phe Trp Thr Leu Arg Tyr
        275                 280                 285

Ser Thr Cys Leu Glu Asp Gly Ser Tyr Val Val Cys Glu Arg Ser Leu
    290                 295                 300
```

-continued

```
Thr Ser Ala Thr Gly Gly Pro Thr Gly Pro Pro Ser Ser Asn Phe Val
305                 310                 315                 320

Arg Ala Glu Met Lys Pro Ser Gly Phe Leu Ile Arg Pro Cys Asp Gly
                325                 330                 335

Gly Gly Ser Ile Leu His Ile Val Asp His Val Asp Leu Asp Ala Trp
            340                 345                 350

Ser Val Pro Glu Val Met Arg Pro Leu Tyr Glu Ser Ser Lys Ile Leu
        355                 360                 365

Ala Gln Lys Met Thr Val Ala Ala Leu Arg His Val Arg Gln Ile Ala
    370                 375                 380

Gln Glu Thr Ser Gly Glu Val Gln Tyr Gly Gly Arg Gln Pro Ala
385                 390                 395                 400

Val Leu Arg Thr Phe Ser Gln Arg Leu Cys Arg Gly Phe Asn Asp Ala
                405                 410                 415

Val Asn Gly Phe Val Asp Asp Gly Trp Ser Pro Met Gly Ser Asp Gly
            420                 425                 430

Ala Glu Asp Val Thr Val Met Ile Asn Leu Ser Pro Gly Lys Phe Gly
        435                 440                 445

Gly Ser Gln Tyr Gly Asn Ser Phe Leu Pro Ser Phe Gly Ser Gly Val
    450                 455                 460

Leu Cys Ala Lys Ala Ser Met Leu Leu Gln Asn Val Pro Pro Ala Val
465                 470                 475                 480

Leu Val Arg Phe Leu Arg Glu His Arg Ser Glu Trp Ala Asp Tyr Gly
                485                 490                 495

Val Asp Ala Tyr Ala Ala Ser Leu Arg Ala Ser Pro Phe Ala Val
        500                 505                 510

Pro Cys Ala Arg Ala Gly Gly Phe Pro Ser Asn Gln Val Ile Leu Pro
    515                 520                 525

Leu Ala Gln Thr Val Glu His Glu Glu Ser Leu Glu Val Val Arg Leu
530                 535                 540

Glu Gly His Ala Tyr Ser Pro Glu Asp Met Gly Leu Ala Arg Asp Met
545                 550                 555                 560

Tyr Leu Leu Gln Leu Cys Ser Gly Val Asp Glu Asn Val Gly Gly
                565                 570                 575

Cys Ala Gln Leu Val Phe Ala Pro Ile Asp Glu Ser Phe Ala Asp Asp
        580                 585                 590

Ala Pro Leu Leu Pro Ser Gly Phe Arg Ile Ile Pro Leu Glu Gln Lys
    595                 600                 605

Ser Thr Pro Asn Gly Ala Ser Ala Asn Arg Thr Leu Asp Leu Ala Ser
610                 615                 620

Ala Leu Glu Gly Ser Thr Arg Gln Ala Gly Glu Ala Asp Pro Asn Gly
625                 630                 635                 640

Cys Asn Phe Arg Ser Val Leu Thr Ile Ala Phe Gln Phe Thr Phe Asp
                645                 650                 655

Asn His Ser Arg Asp Ser Val Ala Ser Met Ala Arg Gln Tyr Val Arg
        660                 665                 670

Ser Ile Val Gly Ser Ile Gln Arg Val Ala Leu Ala Ile Ala Pro Arg
    675                 680                 685

Pro Gly Ser Asn Ile Ser Pro Ile Ser Val Pro Thr Ser Pro Glu Ala
690                 695                 700

Leu Thr Leu Val Arg Trp Ile Ser Arg Ser Tyr Ser Leu His Thr Gly
705                 710                 715                 720

Ala Asp Leu Phe Gly Ser Asp Ser Gln Thr Ser Gly Asp Thr Leu Leu
                725                 730                 735
```

```
His Gln Leu Trp Asn His Ser Asp Ala Ile Leu Cys Cys Ser Leu Lys
                740                 745                 750

Thr Asn Ala Ser Pro Val Phe Thr Phe Ala Asn Gln Thr Gly Leu Asp
        755                 760                 765

Met Leu Glu Thr Thr Leu Val Ala Leu Gln Asp Ile Met Leu Asp Lys
    770                 775                 780

Thr Leu Asp Glu Pro Gly Arg Lys Ala Leu Cys Ser Glu Phe Pro Lys
785                 790                 795                 800

Ile Met Gln Gln Gly Tyr Ala His Leu Pro Ala Gly Val Cys Ala Ser
                805                 810                 815

Ser Met Gly Arg Met Val Ser Tyr Glu Gln Ala Thr Val Trp Lys Val
            820                 825                 830

Leu Glu Asp Asp Glu Ser Asn His Cys Leu Ala Phe Met Phe Val Asn
            835                 840                 845

Trp Ser Phe Val
    850

<210> SEQ ID NO 7
<211> LENGTH: 12
<212> TYPE: PRT
<213> ORGANISM: Artificial sequence
<220> FEATURE:
<223> OTHER INFORMATION: Artificially Synthesized Amino Acid Sequence

<400> SEQUENCE: 7

Asp Leu Asp Leu Asn Leu Ala Pro Pro Met Glu Phe
1               5                   10

<210> SEQ ID NO 8
<211> LENGTH: 11
<212> TYPE: PRT
<213> ORGANISM: Artificial sequence
<220> FEATURE:
<223> OTHER INFORMATION: Artificially Synthesized Amino Acid Sequence

<400> SEQUENCE: 8

Leu Asp Leu Asn Leu Ala Pro Pro Met Glu Phe
1               5                   10

<210> SEQ ID NO 9
<211> LENGTH: 11
<212> TYPE: PRT
<213> ORGANISM: Artificial sequence
<220> FEATURE:
<223> OTHER INFORMATION: Artificially Synthesized Amino Acid Sequence

<400> SEQUENCE: 9

Leu Asp Leu Asn Leu Ala Ala Ala Ala Ala Ala
1               5                   10

<210> SEQ ID NO 10
<211> LENGTH: 10
<212> TYPE: PRT
<213> ORGANISM: Artificial sequence
<220> FEATURE:
<223> OTHER INFORMATION: Artificially Synthesized Amino Acid Sequence

<400> SEQUENCE: 10

Leu Asp Leu Glu Leu Arg Leu Gly Phe Ala
1               5                   10
```

```
<210> SEQ ID NO 11
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 11

Asp Leu Glu Leu Arg Leu
1               5

<210> SEQ ID NO 12
<211> LENGTH: 10
<212> TYPE: PRT
<213> ORGANISM: Artificial sequence
<220> FEATURE:
<223> OTHER INFORMATION: Artificially Synthesized Amino Acid Sequence

<400> SEQUENCE: 12

Leu Asp Leu Gln Leu Arg Leu Gly Tyr Tyr
1               5                   10

<210> SEQ ID NO 13
<211> LENGTH: 7
<212> TYPE: PRT
<213> ORGANISM: Artificial sequence
<220> FEATURE:
<223> OTHER INFORMATION: Artificially Synthesized Amino Acid Sequence

<400> SEQUENCE: 13

Leu Asp Leu Glu Leu Arg Leu
1               5

<210> SEQ ID NO 14
<211> LENGTH: 11
<212> TYPE: PRT
<213> ORGANISM: Artificial sequence
<220> FEATURE:
<223> OTHER INFORMATION: Artificially Synthesized Amino Acid Sequence

<400> SEQUENCE: 14

Leu Asp Leu Glu Leu Ala Ala Ala Ala Ala
1               5                   10

<210> SEQ ID NO 15
<211> LENGTH: 10
<212> TYPE: PRT
<213> ORGANISM: Artificial sequence
<220> FEATURE:
<223> OTHER INFORMATION: Artificially Synthesized Amino Acid Sequence

<400> SEQUENCE: 15

Leu Asp Leu Glu Leu Arg Leu Ala Ala Ala
1               5                   10

<210> SEQ ID NO 16
<211> LENGTH: 8
<212> TYPE: PRT
<213> ORGANISM: Artificial sequence
<220> FEATURE:
<223> OTHER INFORMATION: Artificially Synthesized Amino Acid Sequence

<400> SEQUENCE: 16

Leu Asp Leu Glu Leu Arg Leu Gly
1               5
```

```
<210> SEQ ID NO 17
<211> LENGTH: 11
<212> TYPE: PRT
<213> ORGANISM: Artificial sequence
<220> FEATURE:
<223> OTHER INFORMATION: Artificially Synthesized Amino Acid Sequence

<400> SEQUENCE: 17

Phe Asp Leu Asn Phe Ala Pro Leu Asp Cys Val
1               5                   10

<210> SEQ ID NO 18
<211> LENGTH: 11
<212> TYPE: PRT
<213> ORGANISM: Artificial sequence
<220> FEATURE:
<223> OTHER INFORMATION: Artificially Synthesized Amino Acid Sequence

<400> SEQUENCE: 18

Phe Asp Leu Asn Ile Pro Pro Ile Pro Glu Phe
1               5                   10

<210> SEQ ID NO 19
<211> LENGTH: 13
<212> TYPE: PRT
<213> ORGANISM: Artificial sequence
<220> FEATURE:
<223> OTHER INFORMATION: Artificially Synthesized Amino Acid Sequence

<400> SEQUENCE: 19

Phe Gln Phe Asp Leu Asn Phe Pro Pro Leu Asp Cys Val
1               5                   10

<210> SEQ ID NO 20
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 20

Asp Leu Asp Leu Arg Leu
1               5

<210> SEQ ID NO 21
<211> LENGTH: 35
<212> TYPE: PRT
<213> ORGANISM: Artificial sequence
<220> FEATURE:
<223> OTHER INFORMATION: Artificially Synthesized Amino Acid Sequence

<400> SEQUENCE: 21

Val Gly Pro Thr Val Ser Asp Ser Ser Ser Ala Val Glu Glu Asn Gln
1               5                   10                  15

Tyr Asp Gly Lys Arg Gly Ile Asp Leu Asp Leu Asn Leu Ala Pro Pro
                20                  25                  30

Met Glu Phe
        35

<210> SEQ ID NO 22
<211> LENGTH: 11
<212> TYPE: PRT
<213> ORGANISM: Artificial sequence
<220> FEATURE:
<223> OTHER INFORMATION: Artificially Synthesized Amino Acid Sequence
```

```
<400> SEQUENCE: 22

Asp Leu Asp Leu Glu Leu Arg Leu Gly Phe Ala
1               5                   10

<210> SEQ ID NO 23
<211> LENGTH: 12
<212> TYPE: PRT
<213> ORGANISM: Artificial sequence
<220> FEATURE:
<223> OTHER INFORMATION: Artificially Synthesized Amino Acid Sequence

<400> SEQUENCE: 23

Leu Asp Leu Asp Leu Glu Leu Arg Leu Gly Phe Ala
1               5                   10

<210> SEQ ID NO 24
<211> LENGTH: 204
<212> TYPE: PRT
<213> ORGANISM: Arabidopsis thaliana

<400> SEQUENCE: 24

Met Glu Arg Ser Asn Ser Ile Glu Leu Arg Asn Ser Phe Tyr Gly Arg
1               5                   10                  15

Ala Arg Thr Ser Pro Trp Ser Tyr Gly Asp Tyr Asp Asn Cys Gln Gln
                20                  25                  30

Asp His Asp Tyr Leu Leu Gly Phe Ser Trp Pro Pro Arg Ser Tyr Thr
            35                  40                  45

Cys Ser Phe Cys Lys Arg Glu Phe Arg Ser Ala Gln Ala Leu Gly Gly
        50                  55                  60

His Met Asn Val His Arg Arg Asp Arg Ala Arg Leu Arg Leu Gln Gln
65                  70                  75                  80

Ser Pro Ser Ser Ser Thr Pro Ser Pro Tyr Pro Asn Pro Asn
                85                  90                  95

Tyr Ser Tyr Ser Thr Met Ala Asn Ser Pro Pro His His Ser Pro
                100                 105                 110

Leu Thr Leu Phe Pro Thr Leu Ser Pro Pro Ser Ser Pro Arg Tyr Arg
            115                 120                 125

Ala Gly Leu Ile Arg Ser Leu Ser Pro Lys Ser Lys His Thr Pro Glu
        130                 135                 140

Asn Ala Cys Lys Thr Lys Lys Ser Ser Leu Leu Val Glu Ala Gly Glu
145                 150                 155                 160

Ala Thr Arg Phe Thr Ser Lys Asp Ala Cys Lys Ile Leu Arg Asn Asp
                165                 170                 175

Glu Ile Ile Ser Leu Glu Leu Glu Ile Gly Leu Ile Asn Glu Ser Glu
            180                 185                 190

Gln Asp Leu Asp Leu Glu Leu Arg Leu Gly Phe Ala
        195                 200

<210> SEQ ID NO 25
<211> LENGTH: 30
<212> TYPE: PRT
<213> ORGANISM: Arabidopsis thaliana

<400> SEQUENCE: 25

Asn Asp Glu Ile Ile Ser Leu Glu Leu Glu Ile Gly Leu Ile Asn Glu
1               5                   10                  15

Ser Glu Gln Asp Leu Asp Leu Glu Leu Arg Leu Gly Phe Ala
                20                  25                  30
```

```
<210> SEQ ID NO 26
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 26

Asp Leu Asn Leu Arg Leu
1               5

<210> SEQ ID NO 27
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 27

Asp Leu Asp Leu Arg Leu
1               5

<210> SEQ ID NO 28
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 28

Asp Leu Gln Leu Arg Leu
1               5

<210> SEQ ID NO 29
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 29

Asp Leu Arg Leu Arg Leu
1               5

<210> SEQ ID NO 30
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 30

Glu Leu Glu Leu Arg Leu
1               5

<210> SEQ ID NO 31
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 31

Asn Leu Glu Leu Arg Leu
1               5
```

```
<210> SEQ ID NO 32
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 32

Gln Leu Glu Leu Arg Leu
1               5

<210> SEQ ID NO 33
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 33

Asp Leu Glu Leu Asn Leu
1               5

<210> SEQ ID NO 34
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 34

Asp Leu Glu Leu Gln Leu
1               5

<210> SEQ ID NO 35
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 35

Thr Leu Glu Leu Arg Leu
1               5

<210> SEQ ID NO 36
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 36

Asp Leu Glu Leu Thr Leu
1               5

<210> SEQ ID NO 37
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 37

Ser Leu Glu Leu Arg Leu
1               5
```

```
<210> SEQ ID NO 38
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 38

Asp Leu Glu Leu Ser Leu
1               5

<210> SEQ ID NO 39
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 39

Asp Leu Thr Leu Arg Leu
1               5

<210> SEQ ID NO 40
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 40

Asp Leu Ser Leu Arg Leu
1               5

<210> SEQ ID NO 41
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 41

Asp Leu His Leu Arg Leu
1               5

<210> SEQ ID NO 42
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 42

Ser Leu Asp Leu His Leu
1               5

<210> SEQ ID NO 43
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 43

Asp Leu Thr Leu Lys Leu
1               5
```

<210> SEQ ID NO 44
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 44

Asp Leu Ser Leu Lys Leu
1               5

<210> SEQ ID NO 45
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 45

Asp Leu Glu Phe Arg Leu
1               5

<210> SEQ ID NO 46
<211> LENGTH: 6
<212> TYPE: PRT
<213> ORGANISM: Artificial sequence
<220> FEATURE:
<223> OTHER INFORMATION: Artificially Synthesized Amino Acid Sequence

<400> SEQUENCE: 46

Asp Phe Glu Leu Arg Leu
1               5

<210> SEQ ID NO 47
<211> LENGTH: 25
<212> TYPE: DNA
<213> ORGANISM: Artificial sequence
<220> FEATURE:
<223> OTHER INFORMATION: Artificially Synthesized Primer Sequence

<400> SEQUENCE: 47
agttagttac ttaagcttgg gcccc                                      25

<210> SEQ ID NO 48
<211> LENGTH: 30
<212> TYPE: DNA
<213> ORGANISM: Artificial sequence
<220> FEATURE:
<223> OTHER INFORMATION: Artificially Synthesized Primer Sequence

<400> SEQUENCE: 48
gatccagtaa gcttaattgg ttccggcgcc                                 30

<210> SEQ ID NO 49
<211> LENGTH: 23
<212> TYPE: DNA
<213> ORGANISM: Artificial sequence
<220> FEATURE:
<223> OTHER INFORMATION: Artificially Synthesized Primer Sequence

<400> SEQUENCE: 49
tagaattcgc ggccgcactc gag                                        23

<210> SEQ ID NO 50
<211> LENGTH: 31
<212> TYPE: DNA
<213> ORGANISM: Artificial sequence

```
<220> FEATURE:
<223> OTHER INFORMATION: Artificially Synthesized Primer Sequence

<400> SEQUENCE: 50
gagaattcgg gccagagctg cagctggatg g                                   31

<210> SEQ ID NO 51
<211> LENGTH: 82
<212> TYPE: DNA
<213> ORGANISM: Artificial sequence
<220> FEATURE:
<223> OTHER INFORMATION: Artificially Synthesized DNA Sequence

<400> SEQUENCE: 51
ctagaggatc cacaattacc aacaacaaca aacaacaaac aacattacaa ttacagatcc    60
cgggggtacc gtcgacgagc tc                                             82

<210> SEQ ID NO 52
<211> LENGTH: 73
<212> TYPE: DNA
<213> ORGANISM: Artificial sequence
<220> FEATURE:
<223> OTHER INFORMATION: Artificially Synthesized DNA Sequence

<400> SEQUENCE: 52
cgtcgacggt accccgggga tctgtaattg taatgttgtt tgttgtttgt tgttgttggt    60
aattgtggat cct                                                       73

<210> SEQ ID NO 53
<211> LENGTH: 43
<212> TYPE: DNA
<213> ORGANISM: Artificial sequence
<220> FEATURE:
<223> OTHER INFORMATION: Artificially Synthesized DNA Sequence

<400> SEQUENCE: 53
gggcttgatc tggatctaga actccgtttg gtttcgctt aag                       43

<210> SEQ ID NO 54
<211> LENGTH: 47
<212> TYPE: DNA
<213> ORGANISM: Artificial sequence
<220> FEATURE:
<223> OTHER INFORMATION: Artificially Synthesized DNA Sequence

<400> SEQUENCE: 54
tcgacttaag cgaaacccaa acggagttct agatccagat caagccc                  47

<210> SEQ ID NO 55
<211> LENGTH: 28
<212> TYPE: DNA
<213> ORGANISM: Artificial sequence
<220> FEATURE:
<223> OTHER INFORMATION: primer

<400> SEQUENCE: 55
atgtctatgg aaggtgtttt tcagagaa                                       28

<210> SEQ ID NO 56
<211> LENGTH: 30
<212> TYPE: DNA
<213> ORGANISM: Artificial sequence
<220> FEATURE:
<223> OTHER INFORMATION: primer
```

```
<400> SEQUENCE: 56
tttctcgtgc caatctggtc tgcctaatgt                                    30

<210> SEQ ID NO 57
<211> LENGTH: 26
<212> TYPE: DNA
<213> ORGANISM: Artificial sequence
<220> FEATURE:
<223> OTHER INFORMATION: primer

<400> SEQUENCE: 57
atgtctatgt cgtctatgtc cccttc                                        26

<210> SEQ ID NO 58
<211> LENGTH: 30
<212> TYPE: DNA
<213> ORGANISM: Artificial sequence
<220> FEATURE:
<223> OTHER INFORMATION: primer

<400> SEQUENCE: 58
ataaggagtc acaccaacgt tagcagctgc                                    30

<210> SEQ ID NO 59
<211> LENGTH: 29
<212> TYPE: DNA
<213> ORGANISM: Artificial sequence
<220> FEATURE:
<223> OTHER INFORMATION: primer

<400> SEQUENCE: 59
atgatgatgg tccattcgat gagcagaga                                     29

<210> SEQ ID NO 60
<211> LENGTH: 30
<212> TYPE: DNA
<213> ORGANISM: Artificial sequence
<220> FEATURE:
<223> OTHER INFORMATION: primer

<400> SEQUENCE: 60
aacgaacgac caattcacga acatgaaagc                                    30
```

METHOD FOR PRODUCING PLANT WITH MODIFIED FLOWER MORPHOLOGY

CROSS-REFERENCE TO RELATED APPLICATIONS

This application is the U.S. National Phase under 35 U.S.C. §371 of International Application PCT/JP2008/063973, filed Aug. 4, 2008, which was published in a non-English language, which claims priority to JP Application No. 2007-204253, filed Aug. 6, 2007.

TECHNICAL FIELD

The present invention relates to a method for producing a plant with modified flower morphology and a plant obtained by using this method. In particular, the present invention relates to a method for producing a plant with modified flower morphology by suppressing the function of a transcription factor involved in the polarity determination and a plant obtained by using this method.

BACKGROUND ART

Flower morphology is one of the critical factors in ornamental value of garden plants. The development of a flower begins with differentiation into a flower primordium from an inflorescence meristem. From the floral meristem contained in the flower primordium, four types of flower organs, sepals, petals, stamens and pistils are differentiated. Thereafter, a mature flower is formed as a complex organ containing differentiated flower organs. Plants with modified flower morphology are highly useful in agriculture because they can be utilized in creation of novel garden plants and creation of fruits with a novel morphology.

Thus far, modification of flower morphology of a plant has been generally carried out by cross-breeding in which varieties of plants are crossed. Yet, the conventional cross-breeding requires long periods of time and expertise in order to produce a plant having the intended morphology. Therefore, a method for simply and surely modifying the flower morphology is demanded.

In general, development of flower morphology in higher plants is explained by the ABC model. In this model, it is considered that the flower morphology is modified through transcriptional regulation of Class A, Class B and Class C genes belonging to a MADS-box family (Hajime Sakai, *Molecular genetics of flower morphogenesis*, new edition "Molecular mechanisms of form determination in plants" (Shujunsha) 150-163 (2000)). The MADS-box family genes are genes encoding a transcription factor containing a conserved region called the MADS-box and constitute a gene family composed of 30 or more genes. Examples of the transcription factor include the Class A genes such as APETALA1 (AP1) and APETALA (AP2), the Class B genes such as APETALA3 (AP3) and PISTILLATA (PI) and the Class C genes such as AGAMOUS (AG). Changes in the flower morphology have been confirmed in mutants of these genes.

Meanwhile, a fundamental structure of a leaf of angiosperms, which is relatively flat tissue, can be generally explained in the basis of three axes, namely the proximal-distal, central-lateral and adaxial-abaxial axes. Examples of transcription factors to determine these polarities include the YABBY group such as YABBY1 (YAB1) or YABBY3 (YAB3), the HD group such as PHABULOSA (PHB) and the KANADI group such as KANADI (KAN). It has been known that these factors are involved in determination of the polarity in leaf blades (Non-patent Literatures 1 to 3).

As a method for modifying flower morphology by genetic engineering, the present inventors have thus far found a method using a peptide which converts an arbitrary transcription factor into a transcription repressor (for example, Patent Literatures 1 to 7). This peptide is excised from a Class II ERF (Ethylene Responsive Element Binding Factor) protein or a plant zinc finger protein (for example *Arabidopsis thaliana* SUPERMAN protein or the like) and has an extremely simple structure. And, by introducing a gene encoding a fusion protein (chimeric protein) in which various transcription factors are fused with the above-mentioned peptide into a plant, a transcription factor had been converted to a transcriptional repressor, and the present inventors have successfully produced a plant in which expression of a targeted gene whose transcription is promoted by the transcription factor is suppressed. Specifically, the present inventors have established a method for producing a male-sterile plant and a method for modifying flower morphology, both in which the expression of the AP3 gene or AG gene of *Arabidopsis thaliana*, which gene is the above-mentioned MADS-box family gene, is suppressed by using a repressor capable of binding to a promoter region of the respective gene (Patent Literatures 8 to 9).

However, it is not known that the flower morphology is modified by overexpressing a chimeric repressor in a recombinant plant so as to suppress the function of a transcription factor involved in the polarity determination of a plant organ, which chimeric repressor was obtained by converting the transcription factor (YAB1, KAN or NIB) involved in the polarity determination of a plant leaf into the transcription repressor.

Patent Literature 1: JP 2001-269177 A (disclosed on Oct. 2, 2001)
Patent Literature 2: JP 2001-269178 A (disclosed on Oct. 2, 2001)
Patent Literature 3: JP 2001-292776 A (disclosed on Oct. 2, 2001)
Patent Literature 4: JP 2001-292777 A (disclosed on Oct. 23, 2001)
Patent Literature 5: JP 2001-269176 A (disclosed on Oct. 2, 2001)
Patent Literature 6: JP 2001-269179 A (disclosed on Oct. 2, 2001)
Patent Literature 7: WO03/055903 (disclosed on Jul. 10, 2003)
Patent Literature 8: JP 2005-192483 A (disclosed on Jul. 21, 2005)
Patent Literature 9: JP 2006-42729 A (disclosed on Feb. 16, 2006)
Non-patent Literature 1: Eshed Y, Baum S F, Perea J V, Bowman J L. *Curr Biol*. 2001 Aug. 21; 11(16):1251-60.
Non-patent Literature 2: Eshed Y, Izhaki A, Baum S F, Floyd S K, Bowman J L. *Development* 2004 June; 131(12):2997-3006.
Non-patent Literature 3: Kidner C A, Timmermans M C. *Curr Opin Plant Biol*. 2007 February; 10(1):13-20

DISCLOSURE OF THE INVENTION

Conventionally, any technique for modifying flower morphology by regulating a gene other than the transcription factors of the Classes A, B and C belonging to the MADS-box family related to flower morphology has not been known. Meanwhile, as described above, the transcription factors such as YAB1, YAB3, PHB and KAN are known as transcription factors determining the polarity of a plant, yet their functions for the flower morphology are not known. Nonetheless, it was thought that, if a function of a transcription factor involved in normal morphogenesis of a flower could be suppressed by overexpressing a chimeric protein in which these transcription factors are converted into the transcription repressor in a recombinant plant, modification of the flower morphology might be efficiently carried out, which modification is different from conventional ones by regulation of the common MADS-box family transcription factor(s).

The present invention was made in the light of the above-mentioned problems and an object thereof is to provide a method for simply and surely producing a novel plant with modified flower morphology by suppressing the function of a transcription factor involved in the polarity determination.

In order to solve the above-mentioned problems, the present inventors intensively studied and succeeded in obtaining a method for producing a plant with modified flower morphology, the method comprising the steps of:

obtaining a transformed cell by introducing a chimeric DNA in which a DNA encoding a transcription factor involved in the polarity determination of a plant, which transcription factor will be described later, and a DNA encoding a functional peptide converting the transcription factor into a transcription repressor are fused; and regenerating a transformed plant from the above-mentioned transformed cell; as well as a transformant with modified flower morphology.

Accordingly, the summary of the present invention is as follows. The present invention provides a method for producing a plant with modified flower morphology, the method comprising modifying the flower morphology of a plant by suppressing the function of a transcription factor involved in the polarity determination of a plant.

Further, the present invention provides a method for producing a plant with modified flower morphology, comprising the steps of: obtaining a transformed cell by introducing a chimeric DNA in which a DNA encoding the above-mentioned transcription factor and a DNA encoding the above-mentioned functional peptide; and regenerating a transformed plant from the above-mentioned transformed cell.

Still further, the present invention provides a method for producing a plant with modified flower morphology, wherein the above-mentioned transcription factor is selected from:

(1) a DNA encoding the amino acid sequence of SEQ ID NO: 2;
(2) a DNA comprising the nucleotide sequence of SEQ ID NO: 1;
(3) a DNA encoding an amino acid sequence of SEQ ID NO: 2 including substitution, deletion, insertion, and/or addition of one or several amino acids;
(4) a DNA hybridizing with the DNA consisting of the nucleotide sequence complementary to the nucleotide sequence of SEQ ID NO: 1 under stringent conditions; and
(5) a DNA encoding an amino acid sequence having an identity of not less than 90% to the amino acid sequence of SEQ ID NO: 2.

Further, the present invention provides a method for producing a plant with modified flower morphology, wherein the above-mentioned transcription factor is selected from:

(1) a DNA encoding the amino acid sequence of SEQ ID NO: 4;
(2) a DNA comprising the nucleotide sequence of SEQ ID NO: 3;
(3) a DNA encoding an amino acid sequence of SEQ ID NO: 4 including substitution, deletion, insertion, and/or addition of one or several amino acids;
(4) a DNA hybridizing with the DNA consisting of the nucleotide sequence complementary to the nucleotide sequence of SEQ ID NO: 3 under stringent conditions; and
(5) a DNA encoding an amino acid sequence having an identity of not less than 90% to the amino acid sequence of SEQ ID NO: 4.

Further, the present invention provides a method for producing a plant with modified flower morphology, wherein the above-mentioned transcription factor is selected from:

(1) a DNA encoding the amino acid sequence of SEQ ID NO: 6;
(2) a DNA comprising the nucleotide sequence of SEQ ID NO: 5;
(3) a DNA encoding an amino acid sequence of SEQ ID NO: 6 including substitution, deletion, insertion, and/or addition of one or several amino acids;
(4) a DNA hybridizing with the DNA consisting of the nucleotide sequence complementary to the nucleotide sequence of SEQ ID NO: 5 under stringent conditions; and
(5) a DNA encoding an amino acid sequence having an identity of not less than 90% to the amino acid sequence of SEQ ID NO: 6.

Further, the present invention provides a method for producing a plant with modified flower morphology, wherein the above-mentioned functional peptide is a peptide having the amino acid sequence of any one of the SEQ ID NO: 7 to SEQ ID NO: 46.

Also, the present invention relates to a plant produced by any one of the above-mentioned methods.

The method for producing a plant according to the present invention has, as described above, a structure of modifying flower morphology of a plant by suppressing the function of a transcription factor(s) involved in the polarity determination of a plant, and hence, shows an effect that the function of the above-mentioned transcription factor such as YAB1, KAN1 and PHB can be suppressed and the flower morphology can be easily modified. More particularly, since florist crops which have morphology changes in their petals, pistils or the like can be produced, the present invention has an effect that novel horticultural varieties can be created. Also, in fruit trees, since the morphology of fruits can be changed, it has also an effect that a fruit with a novel morphology can be created. Furthermore, since the flower morphology can be modified more simply and surely than cross-breeding, the present invention has an effect that the labor force can be reduced.

BEST MODE FOR CARRYING OUT THE INVENTION

Figure 1:
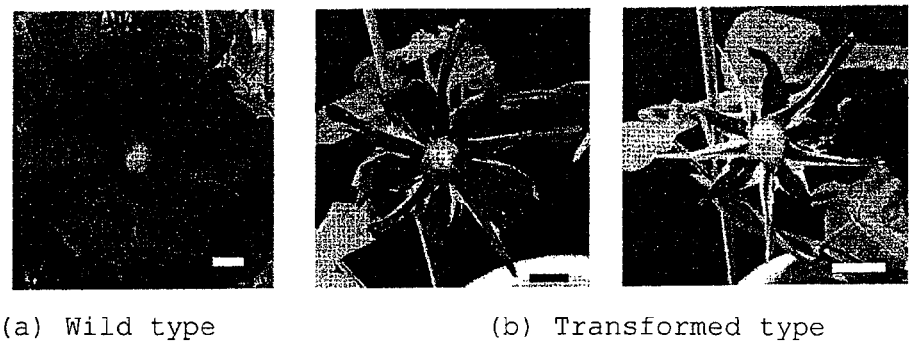
FIG. 1 is photographs showing ATKAN1SRDX transformed morning glory (b) and wild type morning glory (a).

The present invention will be described in detail below; however the present invention is not limited thereto.

A method for suppressing the function of a transcription factor involved in the polarity determination of a plant is not particularly restricted and examples thereof include methods of suppressing the activity of an endogenous transcription factor by introducing a transcription repressor into a plant; and methods of suppressing the expression of a gene encoding a transcription factor by gene disruption, RNA interference (RNAi) or the like. Among these, it is preferred to produce a chimeric protein in a plant, which chimeric protein have been obtained by fusing the above-mentioned transcription factor and a functional peptide converting an arbitrary transcription factor into a transcription repressor. In the thus obtained plant, since the function of the above-mentioned transcription factor is suppressed, a plant with modified flower morphology can be produced. That is, since the above-mentioned transcription factor is indispensable for normal morphogenesis such as the polarity of plant organs (e.g. the upper and lower sides of a leaf and symmetric property), the conversion of the above-mentioned transcription factor into the transcription repressor causes abnormality in the morphogenesis of flower.

In the present method, a gene targeted by the above-mentioned transcription factor needs not to be identified. Since the flower morphology is modified as a result, it is speculated that the above-mentioned target gene is a gene having functions to affect the flower morphology in the process of flower formation. However, in the present method, transcriptional repression can be effectively carried out even without the function and structure of the gene being identified.

In the following description, chimeric proteins used in the method for producing a plant with modified flower morphology according to the present invention; one of the examples of a method for producing a plant according to the present invention; a plant obtained thereby and usefulness thereof; as well as the use thereof will be respectively described.

(I) Construction of Chimeric Protein

As described above, the chimeric protein used in the present invention is a fusion protein in which the above-mentioned transcription factor is fused with the functional peptide converting an arbitrary transcription factor to a transcription repressor. So, the above-mentioned transcription factor and functional peptide will be respectively described.

(I)-1 Transcription Factor Involved in the Polarity Determination of a Plant

Examples of a transcription factor involved in the polarity determination of a plant include the KAN1 protein, KAN2 protein, KAN3 protein, KAN4 protein, YAB1 protein, YAB3 protein and PHB protein of *Arabidopsis thaliana*. As long as it is a transcription factor involved in the polarity determination of a plant, it is not particularly restricted.

A representative example of the transcription factor used in the present invention preferably includes the KAN1 protein, YAB1 protein or PHB protein of *Arabidopsis thaliana*. The KAN1 protein is a protein having the amino acid sequence shown in SEQ ID NO: 2. The YAB1 protein is a protein having the amino acid sequence shown in SEQ ID NO: 4. The PHB protein is a protein having the amino acid sequence shown in SEQ ID NO: 6.

In examples described later, by fusing a functional peptide described later with the KAN1 protein, YAB1 protein or PHB protein, the KAN1 protein, YAB1 protein or PHB protein, each of which is the transcription factor, is converted into a transcription repressor.

However, the above-mentioned transcription factor is not limited to SEQ ID NO: 2, 4 or 6, and may be a homolog having equivalent functions. Specifically, even a protein having an amino acid sequence of SEQ ID NO: 2 including substitution, deletion, insertion, and/or addition of one or several amino acids can be used in the present invention, as long as it is capable of modifying the flower morphology of a plant when introduced into the plant as a chimeric protein with the transcription repressor converting peptide described later. Also, even a protein having an amino acid sequence of SEQ ID NO: 4 including substitution, deletion, insertion, and/or addition of one or several amino acids can be used in the present invention, as long as it is capable of modifying the flower morphology of a plant when introduced into the plant as a chimeric protein with the transcription repressor converting peptide described below. Also, even a protein having an amino acid sequence of SEQ ID NO: 6 including substitution, deletion, insertion, and/or addition of one or several amino acids can be used in the present invention, as long as it is capable of modifying the flower morphology of a plant when introduced into the plant as a chimeric protein with the transcription repressor converting peptide described below.

The range of the term "one or several amino acids" in the above-mentioned phrase "an amino acid sequence of SEQ ID NO: 2, 4 or 6 including substitution, deletion, insertion, or addition of one or several amino acids" is not particularly restricted and means, for example, 1 to 20 amino acids, preferably 1 to 10 amino acids, more preferably 1 to 7 amino acids, further preferably 1 to 5 amino acids, particularly preferably 1 to 3 amino acids.

When the chimeric protein used in the present invention is produced, as described later, a known gene recombination technique can preferably be employed. A gene encoding the above-mentioned transcription factor can be preferably used in the method for producing a plant according to the present invention.

For instance, when the KAN1 protein is used as a transcription factor, a gene encoding this KAN1 protein (for convenience in description, referred to as KAN1 gene) can be exemplified. A specific example of the KAN1 gene includes a polynucleotide containing the nucleotide sequence of SEQ ID NO: 1 as the open reading frame (ORF). Also, for instance, when the YAB1 protein is used as a transcription factor, a gene encoding this YAB1 protein (for convenience in description, referred to as YAB1 gene) can be exemplified. A specific example of the YAB1 gene includes a polynucleotide containing the nucleotide sequence of SEQ ID NO: 3 as the open reading frame (ORF). Also, for instance, when the PHB protein is used as a transcription factor, a gene encoding this PHB protein (for convenience in description, referred to as PHB gene) can be exemplified. A specific example of the PHB gene includes a polynucleotide containing the nucleotide sequence of SEQ ID NO: 5 as the open reading frame (ORF).

Needless to say, a DNA encoding the transcription factor used in the present invention is not limited to the above-mentioned examples and may be a DNA having a homology to the nucleotide sequence of SEQ ID NO: 1, 3 or 5. Specific examples thereof include a DNA hybridizing with the DNA consisting of the nucleotide sequence complementary to the nucleotide sequence of SEQ ID NO: 1, 3 or 5 under stringent conditions and encoding a protein capable of modifying the flower morphology of a plant when introduced into the plant as a chimeric protein with a transcription repressor converting peptide. The term "hybridizing under stringent conditions" herein means preferably binding under conditions of washing with 2×SSC at 60° C., more preferably binding under conditions of washing with 0.1×SSC at 60° C. And, examples of the DNA encoding the transcription factor used in the present invention also include a DNA encoding an amino acid sequence having an identity of not less than 90% to the amino acid sequence of SEQ ID NO: 2, 4 or 6.

The above-mentioned hybridization can be carried out by a conventional known method such as the method described in J. Sambrook et al. *Molecular Cloning A Laboratory Manual*, 2nd Ed, Cold Spring Harbor Laboratory (1989). Usually, the higher the temperature and the lower the concentration of salt, the higher the stringency is (it is more difficult for non-specific DNA to hybridize).

A method for obtaining a DNA encoding the above-mentioned transcription factor is not restricted. The DNA can be isolated from many plants by a conventional known method. For instance, a primer pair prepared on the basis of a nucleotide sequence of a known transcription factor can be used. Using this primer pair, PCR can be carried out with cDNA or genomic DNA of a plant as a template, thereby obtaining the above-mentioned DNA. A DNA encoding the above-mentioned transcription factor can also be obtained by chemical synthesis by a conventional known method.

(I)-2 Functional Peptide Converting Transcription Factor into Transcription Repressor A functional peptide converting an arbitrary transcription factor into a transcription repressor, which peptide is used in the present invention (for convenience in description, referred to as transcription repressor converting peptide), is not particularly restricted. As long as it is a peptide capable of suppressing the function of the corresponding transcription factor by forming a chimeric protein fused with the transcription factor, any peptides can be employed. Specific examples include transcription repressor converting peptides discovered by the present inventors (Patent Literatures 1 to 7).

The present inventors discovered that a protein obtained by binding one of the Class II ERF genes, AtERF3 protein, AtERF4 protein, AtERF7 protein or AtERF8 protein, all of which are derived from *Arabidopsis thaliana*, to a transcription factor converted the transcription factor into a transcription repressor and markedly suppressed the function of the targeted transcription factor. They therefore constructed an effector plasmid containing a DNA encoding each of the above-mentioned protein and a DNA excised therefrom, and actually succeeded in suppressing the function of the transcription factor by introducing this plasmid into plant cells (see, for example, Patent Literatures 1 to 4). Additionally, when the same test as described above was carried out for one of the Class II ERF genes, namely a gene encoding tobacco ERF3 protein (see, for example, Patent Literature 5), a gene encoding rice OsERF3 protein (see, for example, Patent Literature 6) and one of the genes of zinc finger proteins, namely a gene encoding ZAT10 or ZAT11 of *Arabidopsis thaliana*, it was also found that the transcription factor was converted into the transcription repressor to suppress the function of the targeted transcription factor. Furthermore, the present inventors revealed that these proteins had a common motif containing aspartic acid-leucine-asparagine (DLN) in their carboxyl-terminal region. As a result of studying proteins having this common motif they have found that the protein suppressing the function of a transcription factor may be a peptide with an extremely simple structure and these peptides with the extremely simple structure have the function of converting an arbitrary transcription factor into a transcription repressor.

The present inventors have also found that, even though the *Arabidopsis thaliana* SUPERMAN protein has a motif which is not identical to the above-mentioned common motif, it has the function of converting an arbitrary transcription factor to a transcription repressor, as well as that a chimeric DNA obtained by binding a DNA encoding this SUPERMAN protein to a DNA encoding a DNA binding domain of a transcription factor or a transcription factor generates a protein having a strong ability for the transcription repression. (Ohta, M., Matsui, K., Hiratsu, K., Shinshi, H. and Ohme-Takagi, M., *The Plant Cell*, Vol. 13, 1959-1968, August, 2001; Hiratsu, K., Ohta, M., Matsui, K., Ohme-Takagi, M., *FEBS Letters*, 514, 351-354 (2002)).

Hence, one of the examples of the transcription repressor converting peptide used in the present invention, in this embodiment, includes Class II ERF proteins such as the AtERF3 protein, AtERF4 protein, AtERF7 protein and AtERF8 protein, all of which are derived from *Arabidopsis thaliana*, the tobacco ERF3 protein, rice OsERF3 protein, zinc finger proteins such as *Arabidopsis thaliana* ZAT10 protein and ZAT11 protein, *Arabidopsis thaliana* SUPERMAN protein, peptides cut off from these proteins, and synthetic peptides having the above-mentioned function.

More specific examples of the above-mentioned transcription repressor converting peptide include peptides having the amino acid sequence of any one of SEQ ID NOs: 7 to 46. These oligopeptides are those found to be the above-mentioned transcription repressor converting peptide by the present inventors.

(I)-3 Method for Producing Chimeric Protein.

Various transcription repressor converting peptides described in the above (I)-2 can convert the corresponding transcription factor to a transcription repressor by being fused with the transcription factor described in the above (I)-1 to provide a chimeric protein. Therefore, in the present invention, if a polynucleotide encoding the above-mentioned transcription repressor converting peptide is used, and a chimeric DNA in which the polynucleotide is fused with DNA encoding the transcription factor is obtained, the chimeric protein can be produced.

Specifically, by linking a polynucleotide encoding the above-mentioned transcription repressor converting peptide (for convenience in description, referred to as transcription repressor converting polynucleotide) to a DNA encoding the above-mentioned transcription factor, a chimeric DNA is constructed. The chimeric DNA is introduced into plant cells. By this, the chimeric protein can be produced. A specific method for introducing the chimeric DNA into plant cells will be explained in detail in the section (II) described later.

A specific nucleotide sequence of the above-mentioned transcription repressor converting polynucleotide is not restricted. As long as it contains, on the basis of genetic codes, a nucleotide sequence corresponding to the amino acid sequence of the above-mentioned transcription repressor converting peptide, any nucleotide sequence may be employed. Further, as needed, the above-mentioned transcription repressor converting polynucleotide may contain a nucleotide sequence which is a connecting region for linking the polynucleotide to a DNA of the transcription factor. Further, in cases where the amino acid reading frame of the above-mentioned transcription repressor converting polynucleotide is not in-frame with the reading frame of the DNA of the transcription factor, an additional nucleotide sequence for allowing them to be in-frame may be included.

The chimeric protein used in the present invention can be obtained from the above-mentioned chimeric DNA in which a DNA encoding the transcription factor is linked with the transcription repressor converting polynucleotide. Therefore, as long as the above-mentioned chimeric protein contains the above-mentioned transcription factor and the above-mentioned transcription repressor converting peptide, the structure thereof is not restricted. For instance, various additional polypeptides such as a polypeptide having a linker function for linking the transcription factor and the transcription repressor converting peptide, and a polypeptide to label the chimeric protein with an epitope such as His, Myc or Flag, can be contained. Furthermore, in the above-mentioned chimeric protein, a structure other than the polypeptide, such as a sugar chain or isoprenoid group, may be contained as needed. In addition, in the chimeric protein, the order of the transcription factor and the transcription repressor converting peptide is not restricted and either one may be placed on the amino terminal region.

(II) Method for Producing Plants

The method for producing a plant according to the present invention is not restricted as long as it includes processes of producing the chimeric protein described in the above (I) in the plant and modifying the flower morphology. And, if the method for producing a plant according to the present invention is shown with concrete steps, examples include a production method comprising the steps of, for example, constructing an expression vector, transformation and selection. Among these, in the present invention, as long as the method includes at least the step of transformation, any method may be employed. Each of the steps will be concretely described below.

(II)-1 Step of Constructing Expression Vector

The step of constructing an expression vector, which step is carried out in the present invention, is not restricted, as long as it is a step of constructing a recombinant expression vector containing the DNA encoding the transcription factor described in the above (I)-1, the transcription repressor converting polynucleotide described in the above (I)-2 and a promoter.

As a parent vector for the above-mentioned recombinant expression vector, various conventional known vectors can be used. For instance, a plasmid, a phage, a cosmid or the like can be used and the vector can be appropriately selected depending on a plant cell into which the vector is introduced and a method for introduction. Specific examples of the vector include pBR322, pBR325, pUC19, pUC119, pBluescript, pBluescriptSK and the pBI-based vectors. Particularly, in cases where the method for introducing the vector into a plant is a method using *Agrobacterium*, it is preferred to use a pBI-based binary vector. Specific examples of the pBI-based binary vector include pBIG, pBIN19, pBI101, pBI121 and pBI221.

The above-mentioned promoter is not restricted as long as it is a promoter capable of expressing a gene in a plant and a known promoter can preferably be used. Examples of this promoter include the cauliflower mosaic virus 35S promoter (CaMV 35S), an actin promoter, a promoter of a nopaline synthetase gene, the tobacco PR1a gene promoter and the promoter of the small subunit of the tomato ribulose-1,5-bisphosphate carboxylase/oxygenase. Among these, the cauliflower mosaic virus 35S promoter or the actin promoter can more preferably be used. The use of each of the above-mentioned promoters enables the obtained recombinant expression vector to strongly express an arbitrary gene when introduced in plant cells.

As long as the above-mentioned promoter is linked such that a chimeric DNA in which a DNA encoding the transcription factor is linked to the transcription repressor converting polynucleotide can be expressed and introduced in the vector, a specific structure as a recombinant expression vector is not restricted.

The above-mentioned recombinant expression vector may further contain another DNA segment, in addition to the above-mentioned promoter and the above-mentioned chimeric DNA. The other DNA segment is not restricted and examples thereof include terminators, selection makers, enhancers and nucleotide sequences to enhance translational efficiency. Also, the above-mentioned recombinant expression vector may further have a T-DNA region. The T-DNA region can increase the efficiency of gene introduction particularly when the above-mentioned recombinant expression vector is introduced into plants using *Agrobacterium*.

The terminator is not restricted as long as it has a function as a transcription termination site, and a known terminator may be used. For instance, specifically, a transcription termination region of a nopaline synthetase gene (Nos terminator), the transcription termination region of the cauliflower mosaic virus 35S (CaMV 35S terminator) or the like can preferably be used. Among these, the Nos terminator can more preferably be used.

In the above-mentioned vector for transformation, by placing the terminator on an appropriate site, a phenomenon that an unnecessarily long transcription product is synthesized, or that a strong promoter decreases the number of copies of plasmid can be prevented from occurring after the introduction in plant cells.

As the above-mentioned selection marker, for example, a drug resistance gene can be used. One of the specific examples of this drug-resistant gene includes drug resistance genes against hygromycin, bleomycin, kanamycin, gentamicin, chloramphenicol or the like. By this, selection of a plant growing in a medium containing the above-mentioned antibiotics allows a transformed plant to be readily selected.

A method for constructing the above-mentioned recombinant expression vector is also not restricted. The above-mentioned promoter, a DNA encoding the transcription factor, the transcription repressor converting polynucleotide and, as needed, the above-mentioned other DNA segment may be incorporated into an appropriately selected parent vector in a prescribed order. For instance, a DNA encoding the transcription factor may be linked with the transcription repressor converting polynucleotide to construct a chimeric DNA; and then this chimeric DNA may be linked with the promoter (and, as needed, terminator or the like) to construct an expression cassette, which may be introduced into the vector.

In the construction of the chimeric DNA and the construction of the expression cassette, the order of these DNA segments can be defined by, for example, preparing digestion sites of respective DNA segments as a cohesive ends which are complement to each other and allowing them to react using a ligation enzyme. In cases where a terminator is included in the expression cassette, any order is acceptable as long as the order is, from the upstream, a promoter, the above-mentioned chimeric DNA and a terminator. Also, reagents for constructing the recombinant expression vector, that is, the types of restriction enzymes, ligation enzymes and the like are not restricted and commercially available reagents may be appropriately selected and used.

A method for propagating (a method for producing) the above-mentioned recombinant expression vector is also not particularly restricted and a conventional known method can be employed. In general, using *E. coli* as a host, the vector may be propagated in the *E. coli*. In this case, a preferred type of *E. coli* may be selected depending on the type of the vector.

(II)-2 Step of Transformation

Any step of transformation is acceptable as long as the step carried out in the present invention comprises introducing the recombinant expression vector described in the above-mentioned (II)-1 into plants cells and producing the chimeric protein described in the above-mentioned (I).

A method for introducing the above-mentioned recombinant expression vector in plant cells (a method of transformation) is not restricted and a known method appropriate to the plant cells can be employed. Specific examples include a method using *Agrobacterium* and a method in which the vector is directly introduced into the plant cells. As the method for introducing the recombinant expression vector directly into the plant cells, microinjection method, electroporation method, polyethylene glycol method, particle gun method, protoplast fusion method, calcium phosphate method or the like can be used.

Examples of the plant cells into which the above-mentioned recombinant expression vector is introduced include cells of each tissue in plant organs such as flowers, leaves and roots; callus; adventitious embryos; and cells of suspension culture.

Here, in the method for producing a plant according to the present invention, the above-mentioned recombinant expression vector may be appropriately constructed depending on the type of plants to be produced. A widely usable recombinant expression vector may be constructed in advance and may be introduced into the plant cells.

(II)-3 Step of Selecting and Regenerating Plants

As long as the method for producing a plant according to the present invention includes the above-mentioned step of transformation, any method may be employed. Further, a step of constructing the above-mentioned recombinant expression vector may be included. Furthermore, another step may be included. Specific examples thereof include the step of selection in which an appropriate transformant is selected from plants after the transformation.

The step of selection is not restricted. For instance, the selection may be carried out using drug resistance such as hygromycin resistance or the like as a standard. Or, the selection may be carried out based on the flower morphology of a plant per se, after allowing a transformant to grow. An example of the selection based on the flower morphology includes a method for comparing the flower morphology of the transformant with that of a plant which is not transformed (see examples described later). In particular, the flower morphology not only allows the selection to be carried out merely by a simple comparison but also enables the modification of flower morphology, which is the very effect of the present invention, to be confirmed.

A desired transformed plant can be obtained by breeding and growing tissues such as cells, adventitious buds or adventitious embryos selected in the above-mentioned step of selection.

Confirmation whether the above-mentioned chimeric DNA in which a DNA encoding a desired transcription factor and a DNA encoding the transcription repressor converting polynucleotide are linked is incorporated into the transformed plant obtained in the above-mentioned step can be carried out by extracting DNA from these tissues according to a conventional method followed by known PCR (Polymerase Chain Reaction) method or Southern hybridization method.

In the present invention, the phrase "flower morphology is modified" is not particularly restricted as long as the character related to the flower morphology is modified. Examples of the flower morphology include the length of a peduncle, the form of petals, the petal pattern, the petal color, the form of the calyx, the form of the pod, the form of the stamen and the form of the pistil; and the morphology of fruits is also included. Yet, the flower morphology is not limited thereto. In addition, the phrase "flower morphology is modified" includes cases where only one morphology is modified and cases where a plurality of morphologies are simultaneously modified.

In the method for producing a plant according to the present invention, because the above-mentioned chimeric DNA is introduced into a plant, a progeny with modified flower morphology can be obtained from the plant by sexual reproduction or asexual reproduction. Also, by obtaining plant cells or breeding materials such as seeds, fruits, stocks, calluses, tubers, cut ears, clusters from this plant or progeny thereof and using these, the plant can be mass-produced. Therefore, in the method for producing a plant according to the present invention, a step of breeding (a step of mass production) in which a plant after the selection is reproduced may be included.

The term "plant" in the present invention includes at least any one of grown plant individual, plant cells, plant tissues, calluses and seeds. That is, in the present invention, those capable of eventually growing up to a plant individual are all considered to be a plant. And, the above-mentioned plant cells include plant cells with various morphologies. As these plant cells, for example, cells of suspension culture, protoplasts, sections of a leaf and the like are included. By allowing these plant cells to grow or differentiate, a plant can be obtained. Regeneration of a plant from plant cells can be carried out using a conventional known method depending on the type of the plant cells. Therefore, the method for producing a plant according to the present invention may include a step of regeneration in which a plant is regenerated from plant cells.

Here, the specific type of a plant with modified flower morphology according to the present invention is not restricted and an example includes a plant whose usefulness is increased by modification of the flower morphology. This plant may be either an angiosperm or a gymnosperm. As an angiosperm, it may be either a monocotyledon or a dicotyledon; however, a dicotyledon is more preferred. As a dicotyledon, it may be either archichlamydeae or sympetalae. Examples of sympetalae include Gentianales, Solanales, Lamiales, Callitrichales, Plantaginales, Campanulales, Scrophulariales, Rubiales, Dipsacales and Asterales. And, examples of archichlamydeae include Dilleniales, Theales, Malvales, Lecythidales, Nepenthales, Violales, Salicales, Capparales, Ericales, Diapensiales, Ebenales, Primulales, Magnoliales, Laurales, Piperales, Aristolochiales, Illiciales, Nymphaeales, Ranunculales, Papaverales, Trochodendrales, Hamamelidales, Daphniphyllales, Fagales, Caryophyllales, Polygonales, Rosales, Fabales, Proteales, Podostemales, Haloragales, Myrtales, Cornales, Santalales, Rafflesiales, Celastrales, Euphorbiales, Rhamnales, Linales, Sapindales, Geraniales and Apiales.

The present invention will now be concretely described with the illustration of examples thereof. However, the scope of the present invention is not limited thereto. Unless otherwise noted, the following experimental procedures were carried out in accordance with methods described in "Molecular Cloning, 2 nd edition" (J. Sambrook et al., Cold Spring Harbor Laboratory press, 1989).

Examples

Construction of Vector for Constructing Vector for Transformation

A vector for constructing a vector for transformation, p35SG, was constructed according to the following steps (1) to (4).

(1) Each region of attL1 and attL2 on the pENTR vector manufactured by Invitrogen Corporation was amplified by PCR using primers attL1-F (SEQ ID NO: 47), attL1-R (SEQ ID NO: 48), attL2-F (SEQ ID NO: 49) and attL2-R (SEQ ID NO: 50). The obtained attL1 fragment was digested with a restriction enzyme, HindIII and the attL2 fragment was digested with EcoRI, followed by purification. Conditions for the PCR reaction involved a cycle of a denaturing reaction at 94° C. for 1 minute, an annealing reaction at 47° C. for 2 minutes and an extension reaction at 74° C. for 1 minute, which cycle was repeated 25 times. Hereinafter, all PCR reactions were carried out under the same conditions.

(2) The plasmid pBI221 manufactured by Clontech, Inc (USA) was digested with restriction enzymes XbaI and SacI and then the GUS (β-glucuronidase) gene was removed by agarose gel electrophoresis, thereby obtaining a 35S-Nos plasmid fragment DNA containing the cauliflower mosaic virus 35S promoter (in the description below, referred to as CaMV 35S for convenience) and a transcription termination region of the nopaline synthetase (in the description below, referred to as Nos-ter for convenience).

(3) DNA fragments having the following sequences of SEQ ID NOs: 51 and 52 were synthesized. The DNA fragments were, after heated at 90° C. for 2 minutes, heated at 60° C. for 1 hour and kept to be static at room temperature (25° C.) for 2 hours to anneal, thereby forming a double-stranded DNA chain. This was ligated into an XbaI-SacI region of the above-mentioned 35S-Nos plasmid fragment DNA, thereby completing the p35S-Nos plasmid. The DNA fragment having the sequence of SEQ ID NO: 51 or 52 contains a BamHI restriction enzyme site at the 5'-terminus, the omega sequence derived from tobacco mosaic virus to enhance translational efficiency, as well as restriction enzyme sites for SmaI, SalI, and SstI, in the mentioned order.

```
                                          (SEQ ID NO: 51)
5'-ctagaggatccacaattaccaacaacaacaaacaacaaacaacatta caattacagatcccgggggtaccgtcgacgagctc-3'

(SEQ ID NO: 52)
5'-cgtcgacggtaccccgggatctgtaattgtaatgttgtttgttgtt tgttgttgttggtaattgtggatcct-3'
```

(4) This p35S-Nos plasmid was digested with a restriction enzyme, HindIII, and then the above-mentioned attL1 fragment was inserted into the resultant. Further, this was digested with EcoRI and the attL2 fragment was inserted thereinto, thereby completing the vector p35SG.

<Construction of Vector for Construction Incorporating Polynucleotide Encoding Transcription Repressor Converting Peptide>

A vector for construction incorporating a polynucleotide encoding a transcription repressor converting peptide, p35SSRDXG, was constructed according to the following steps (1) to (2).

(1) DNAs having the following sequences, which DNAs were designed so as to encode the 12-amino acid transcription repressor converting peptide LDLDLELRLGFA (SRDX: SEQ ID NO: 23) and to have the termination codon TAA at the 3'-terminus, were synthesized. The DNAs were heated at 70° C. for 10 minutes and then allowed to naturally cool to anneal, thereby providing a double-stranded DNA.

```
                                          (SEQ ID NO: 53)
5'-gggcttgatctggatctagaactccgtttgggtttcgcttaag-3'

(SEQ ID NO: 54)
5'-tcgacttaagcgaaacccaaacggagttctagatccagatcaagcc c-3'
```

(2) The p35SG vector was digested with restriction enzymes SmaI and SalI and, into this region, the above-mentioned double-stranded DNA encoding SRDX was inserted, thereby constructing p35SSRDXG.

<Construction of Vector for Transformation>

A vector for transformation of plant, pBIGCKH, having two att sites for mediating recombination with a DNA fragment sandwiched between the att sites of the vector for construction, was constructed according to the following steps (1) to (3).

(1) pBIG (Becker, D. *Nucleic Acids Res.* 18:203, 1990) provided by Michigan State University in the United States was digested with restriction enzymes HindIII and EcoRI and then GUS and Nos regions were removed by electrophoresis.

(2) The Fragment A of the Gateway (registered trademark) vector conversion system purchased from Invitrogen Corporation was inserted into an EcoRV site in the plasmid pBluscript. This was digested with HindIII-EcoRI and the Fragment A fragment was recovered.

(3) The recovered Fragment A fragment was ligated with the above-mentioned pBIG plasmid fragment thereby constructing pBIGCKH. These can be amplified only in *E. coli* DB3.1 (Invitrogen Corporation) and is resistant to chloramphenicol and kanamycin.

<Incorporation of KAN1 Gene into Vector for Construction>

Into the above-mentioned vector for construction, p35SSRDXG, a gene encoding a transcription factor, KAN1 protein, derived from *Arabidopsis thaliana* was incorporated according to the following steps (1) to (3).

(1) From an *Arabidopsis thaliana* cDNA library, a DNA fragment containing only the coding region of the *Arabidopsis thaliana* KAN1 gene (Gene ID No. AT5G16560) except for its termination codon was amplified by PCR using the following primers.

```
Primer 1 (KAN1-F)
                                          (SEQ ID NO: 55)
5'-atgtctatgg aaggtgtttt tcagagaa-3'

Primer 2 (KAN1-R stopless)
                                          (SEQ ID NO: 56)
5'-tttctcgtgccaatctggtctgcctaatgt-3'
```

The cDNA of the KAN1 gene and the amino acid sequence encoded thereby are shown in SEQ ID NOs: 1 and 2, respectively.

(2) The obtained DNA fragment of the KAN1 coding region was ligated to the SmaI site of the vector for construction, p35SSRDXG, which had been digested with restriction enzyme SmaI in advance.

(3) *E. coli* was transformed with the resulting plasmid. And then, the plasmid was prepared and its nucleotide sequence was determined. A clone having the insert in the forward direction was isolated, thereby obtaining p35SKAN1SRDXG having a chimeric gene with SRDX.

<Incorporation of YAB1 Gene into Vector for Construction>

Into the above-mentioned vector for construction, p35SSRDXG, a gene encoding a transcription factor, YAB1 protein, derived from *Arabidopsis thaliana* was incorporated according to the following steps (1) to (3).

(1) From an *Arabidopsis thaliana* cDNA library, a DNA fragment containing only the coding region of the *Arabidopsis thaliana* YAB1 gene (Gene ID No. AT2G45190) except for its termination codon was amplified by PCR using the following primers.

```
Primer 1 (YAB1-F)
                                          (SEQ ID NO: 57)
5'-atgtctatgt cgtctatgtc cccttc-3'

Primer 2 (YAB1-R stopless)
                                          (SEQ ID NO: 58)
5'-ataagga gtcacaccaacgttagcagctgc-3'
```

The cDNA of the YAB1 gene and the amino acid sequence encoded thereby are shown in SEQ ID NOs: 3 and 4, respectively.

(2) The obtained DNA fragment of the YAB1 coding region was ligated to the SmaI site of the vector for construction, p35SSRDXG, which had been digested with restriction enzyme SmaI in advance.

(3) E. coli was transformed with the resulting plasmid. And then the plasmid was prepared and its nucleotide sequence was determined. A clone having the insert in a forward direction was isolated, thereby obtaining p35SYAB1SRDXG having a chimeric gene with SRDX.

<Incorporation of PHB Gene into Vector for Construction>

Into the above-mentioned vector for construction, p35SSRDXG, a gene encoding a transcription factor, PHB protein derived from *Arabidopsis thaliana* was incorporated according to the following steps (1) to (3).

(1) From an *Arabidopsis thaliana* cDNA library, a DNA fragment containing only the coding region of *Arabidopsis thaliana* PHB gene (Gene ID No. AT2G34710) except for its termination codon was amplified using the following primers by PCR.

```
Primer 1 (PHB-F)
                                        (SEQ ID NO: 59)
5'-atgatgatgg tccattcgatgagcagaga-3'

Primer 2 (PHB-R stopless)
                                        (SEQ ID NO: 60)
5'-aacgaacgaccaattcacgaacatgaaagc-3'
```

The cDNA of the PHB gene and the amino acid sequence encoded thereby are shown in SEQ ID NOs: 5 and 6, respectively.

(2) The obtained DNA fragment of the PHB coding region was ligated to the SmaI site of the vector for construction, p35SSRDXG, which had been digested with restriction enzyme SmaI in advance.

(3) E. coli was transformed with the resulting plasmid. And then the plasmid was prepared and its nucleotide sequence was determined. A clone having the insert in a forward direction was isolated, thereby obtaining p35SPHBSRDXG having a chimeric gene with SRDX.

<Construction of Recombinant Expression Vector>

A DNA fragment containing the CaMV 35S promoter, the chimeric gene, the Nos-ter, and the like on the above-mentioned vector for construction was transferred to a vector for transformation of plant, pBIGCKH, thereby constructing an expression vector for a plant as a host. A recombination reaction was carried out using Gateway (registered trademark) LR clonase (registered trademark) produced by Invitrogen Corporation according to the following the steps (1) to (3).

(1) First, to p35SKAN1 SRDXG, p35SYAB1SRDXG or p35SPHBSRDXG (1.5 µL each (about 300 ng)) and pBIGCKH (4.0 µL (about 600 ng)), 5-fold diluted LR buffer (4.0 µL) and TE buffer (10 mM TrisCl pH 7.0, 1 mM EDTA) (5.5 µL) were added.

(2) To this solution, LR clonase (4.0 µL) was added. The mixture was incubated at 25° C. for 60 minutes. Subsequently, proteinase K (2 µL) was added and the mixture was incubated at 37° C. for 10 minutes.

(3) Thereafter, 1 to 2 µL of this solution was transformed into E. coli (DH5α or the like) and selection was carried out using kanamycin.

By this, a vector for transformation of plant, p35SATKAN1 SRDX, p35SATYAB1SRDX and p35SATPHBSRDX were obtained.

<Introduction of Chimeric Gene into Tissue of Morning Glory>

Immature fruits of morning glory (variety: Violet) at 2 weeks after flowering were immersed in sodium hypochlorite solution with 2% effective chlorine concentration for 15 minutes to be sterilized. Thereafter, immature embryos with a length of 2 mm to 8 mm were removed and placed on an MS basal medium, sucrose (6%), naphthaleneacetic acid (NAA) (3 mg/L) and gelangum (0.2%) (pH 5.8). They were cultured at 25° C. under light conditions, thereby forming adventitious embryos, which were used as tissues for gene transfer.

To the culture broth obtained by culturing *Agrobacterium tumefaciens* (p35SLBA4404-ATKAN1 SRDX, p35SLBA4404-ATYAB1SRDX, p35SLBA4404-ATPHB-SRDX) harboring the vectors for transformation p35SATKANSRDX, p35SATYABSRDX and p35SATPHBSRDX, all of which were obtained above, in the LB medium at 28° C. overnight, the above-mentioned adventitious embryos of morning glory (100 embryos) were immersed and treated for 5 minutes. After the immersion treatment, the resulting embryos were placed on a solid medium prepared by adding sucrose (6%), and NAA (0.5 mg/l) as a plant hormone and acetosyringone 10 (mg/l) to the MS basal medium, adjusting the pH of the mixture to 5.8 and then adding Gelrite (0.2%). Co-culturing was carried out under a temperature condition of 25° C. in the dark for 2 days.

The adventitious embryos (100 embryos) after the co-culturing were place on a solid selection medium prepared by adding sucrose (6%), NAA (0.5 mg/l) as a plant hormone, Augmentin ((manufactured by SmithKline Beecham, Tanabe) containing amoxicillin (250 mg/l), potassium clavulanate (50 mg/l)) and kanamycin (25 mg/l) to the MS medium, adjusting the pH of the mixture to 5.8 and then adding Gelrite (0.2%). They were cultured under a temperature condition of 25° C. in the dark and transferred to a fresh selection medium every month.

<Regeneration of Transformed Morning Glory>

One month after the transfer to the above-mentioned selection medium, the above-mentioned adventitious embryos were placed on a solid regeneration medium prepared by adding sucrose (3%), IAA (2 mg/l) and BA (2 mg/l) as plant hormones, Augmentin ((manufactured by SmithKline Beecham, Tanabe) containing amoxicillin (250 mg/l) and potassium clavulanate (50 mg/l)) and kanamycin (25 mg/l) to the MS medium, adjusting the pH of the mixture to 5.8 and then adding agar (1.2%).

About 2 months after the transfer to the regeneration medium, transformed plants were regenerated from the transformed adventitious embryos. These regenerated plants were placed on a growth medium prepared by adding Augmentin ((manufactured by SmithKline Beecham, Tanabe) containing amoxicillin (250 mg/l), potassium clavulanate (50 mg/l)), and kanamycin (25 mg/l) to an MS medium with a ½ concentration of inorganic salts, adjusting the pH of the mixture to 5.8 and then adding agar (1.2%).

They were cultured under a temperature condition of 25° C. and light conditions (1000 lux, 16-hour illumination). As a result, 25 individuals of morning glory plants transformed with ATKAN1SRDX, 11 individuals of morning glory plants transformed with ATYAB1SRDX and 25 individuals of morning glory plants transformed with ATPHBSRDX were obtained.

All of these plants were acclimatized and potted.

Introduction of the ATKAN1SRDX, ATYAB1SRDX, and ATPHBSRDX genes was confirmed by PCR using a leaf of the thus obtained transformed plant as a material for gene analysis.

In addition, using leaves of 25 individuals of morning glory plants transformed with ATKAN1 SRDX, 11 individuals of morning glory plants transformed with ATYAB1SRDX and 25 individuals of morning glory plants transformed with ATPHBSRDX, all of which transformed morning glory plants were potted above, expression of each chimeric gene in the plant was analyzed by reverse transcription PCR(RT-PCR: a known method) and, as a result, the expression was confirmed in all of the transformant The results of comparison between the phenotype of the morning glory transformed with ATKAN1SRDX and that of the wild type are shown in FIG. 1. FIG. 1 shows the morphology of petals. In FIG. 1, (a) is the wild type plant whereas (b) is the plant transformed with ATKAN1SRDX. As is evident from FIG. 1, the morning glory transformed with ATKAN1SRDX had petals with more severe irregularities, as compared with the wild type, and star-shaped flowering.

Figure 2:
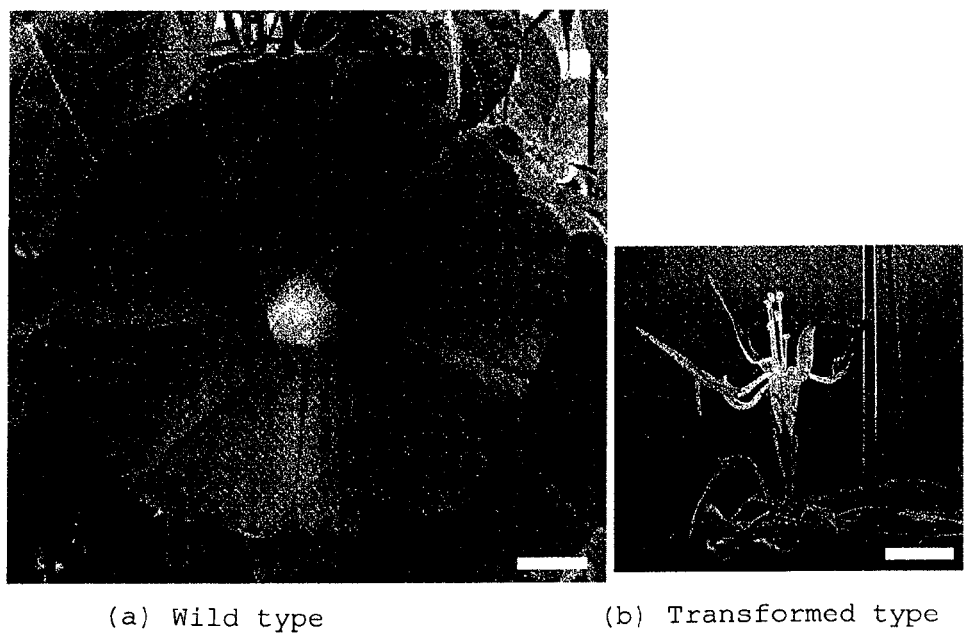
FIG. 2 is photographs showing ATYAB1 SRDX transformed morning glory (b) and wild type morning glory (a).

The results of comparison between the phenotype of the morning glory transformed with ATYAB1SRDX and that of the wild type are shown in FIG. 2. FIG. 2 shows the morphology and the size of petals. In FIG. 2, (a) is the wild type plant whereas (b) is the plant transformed with ATYAB1SRDX. As is evident from FIG. 2, the morning glory transformed with ATYAB1SRDX had petals with more severe irregularities, as compared with the wild type, and star-shaped flowering. Further, the morning glory transformed with ATYAB1 SRDX had smaller petals with a reduced size as compared with the wild type.

Figure 3:
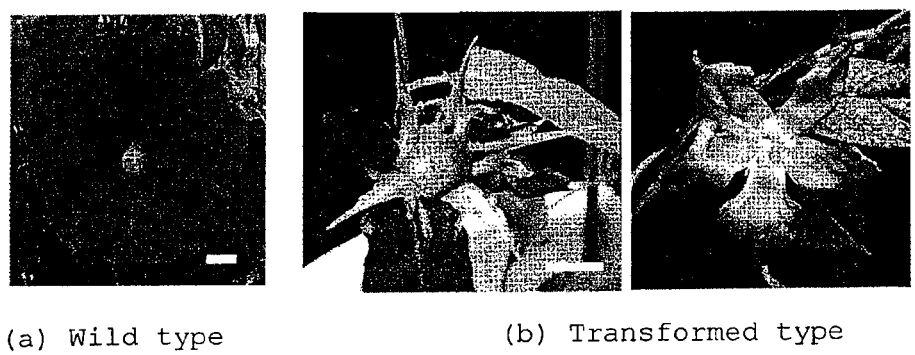
FIG. 3 is photographs showing ATPHBSRDX transformed morning glory (b) and wild type morning glory (a).

The results of comparison between the phenotype of the morning glory transformed with ATPHBSRDX and that of the wild type are shown in FIG. 3. FIG. 3 shows the morphology of petals. In FIG. 3, (a) is the wild type plant whereas (b) is the plant transformed with ATPHBSRDX. As is evident from FIG. 3, the morning glory transformed with ATPHBSRDX had petals with more severe irregularities, as compared with the wild type, and star-shaped flowering.

[Explanation of Sequence Listing]

SEQ ID NO: 1: Nucleotide sequence encoding the KAN1 protein
SEQ ID NO: 2: Amino acid sequence of the KAN1 protein
SEQ ID NO: 3: Nucleotide sequence encoding the YAB1 protein
SEQ ID NO: 4: Amino acid sequence of the YAB1 protein
SEQ ID NO: 5: Nucleotide sequence encoding the PHB protein
SEQ ID NO: 6: Amino acid sequence of the PHB protein
SEQ ID NO: 7: Amino acid sequence of a transcription repressor converting peptide
SEQ ID NO: 8: Amino acid sequence of a transcription repressor converting peptide
SEQ ID NO: 9: Amino acid sequence of a transcription repressor converting peptide
SEQ ID NO: 10: Amino acid sequence of a transcription repressor converting peptide
SEQ ID NO: 11: Amino acid sequence of a transcription repressor converting peptide
SEQ ID NO: 12: Amino acid sequence of a transcription repressor converting peptide
SEQ ID NO: 13: Amino acid sequence of a transcription repressor converting peptide
SEQ ID NO: 14: Amino acid sequence of a transcription repressor converting peptide
SEQ ID NO: 15: Amino acid sequence of a transcription repressor converting peptide
SEQ ID NO: 16: Amino acid sequence of a transcription repressor converting peptide
SEQ ID NO: 17: Amino acid sequence of a transcription repressor converting peptide
SEQ ID NO: 18: Amino acid sequence of a transcription repressor converting peptide
SEQ ID NO: 19: Amino acid sequence of a transcription repressor converting peptide
SEQ ID NO: 20: Amino acid sequence of a transcription repressor converting peptide
SEQ ID NO: 21: Amino acid sequence of a transcription repressor converting peptide
SEQ ID NO: 22: Amino acid sequence of a transcription repressor converting peptide
SEQ ID NO: 23: Amino acid sequence of a transcription repressor converting peptide
SEQ ID NO: 24: Amino acid sequence of a transcription repressor converting peptide
SEQ ID NO: 25: Amino acid sequence of a transcription repressor converting peptide
SEQ ID NO: 26: Amino acid sequence of a transcription repressor converting peptide
SEQ ID NO: 27: Amino acid sequence of a transcription repressor converting peptide
SEQ ID NO: 28: Amino acid sequence of a transcription repressor converting peptide
SEQ ID NO: 29: Amino acid sequence of a transcription repressor converting peptide
SEQ ID NO: 30: Amino acid sequence of a transcription repressor converting peptide
SEQ ID NO: 31: Amino acid sequence of a transcription repressor converting peptide
SEQ ID NO: 32: Amino acid sequence of a transcription repressor converting peptide
SEQ ID NO: 33: Amino acid sequence of a transcription repressor converting peptide
SEQ ID NO: 34: Amino acid sequence of a transcription repressor converting peptide
SEQ ID NO: 35: Amino acid sequence of a transcription repressor converting peptide
SEQ ID NO: 36: Amino acid sequence of a transcription repressor converting peptide
SEQ ID NO: 37: Amino acid sequence of a transcription repressor converting peptide
SEQ ID NO: 38: Amino acid sequence of a transcription repressor converting peptide
SEQ ID NO: 39: Amino acid sequence of a transcription repressor converting peptide
SEQ ID NO: 40: Amino acid sequence of a transcription repressor converting peptide
SEQ ID NO: 41: Amino acid sequence of a transcription repressor converting peptide
SEQ ID NO: 42: Amino acid sequence of a transcription repressor converting peptide
SEQ ID NO: 43: Amino acid sequence of a transcription repressor converting peptide
SEQ ID NO: 44: Amino acid sequence of a transcription repressor converting peptide
SEQ ID NO: 45: Amino acid sequence of a transcription repressor converting peptide
SEQ ID NO: 46: Amino acid sequence of a transcription repressor converting peptide
SEQ ID NO: 47: Forward primer for amplifying the attL1 region
SEQ ID NO: 48: Reverse primer for amplifying the attL1 region
SEQ ID NO: 49: Forward primer for amplifying the attL2 region SEQ ID NO: 50: Reverse primer for amplifying the attL2 region
SEQ ID NO: 51: Oligonucleotide (sense strand) containing BamHI restriction enzyme site, the omega sequence derived from tobacco mosaic virus and restriction enzyme sites of SmaI, SalI and SstI
SEQ ID NO: 52: Oligonucleotide (antisense strand) containing BamHI restriction enzyme site, the omega sequence derived from tobacco mosaic virus and restriction enzyme sites of SmaI, SalI and SstI
SEQ ID NO: 53: Oligonucleotide (sense strand) encoding the transcription repressor converting peptide SRDX
SEQ ID NO: 54: Oligonucleotide (antisense strand) encoding the transcription repressor converting peptide SRDX
SEQ ID NO: 55: Forward primer for amplifying KAN1
SEQ ID NO: 56: Reverse primer for amplifying KAN1
SEQ ID NO: 57: Forward primer for amplifying YAB1
SEQ ID NO: 58: Reverse primer for amplifying YAB1
SEQ ID NO: 59: Forward primer for amplifying PHB
SEQ ID NO: 60: Reverse primer for amplifying PHB

INDUSTRIAL APPLICABILITY

In the present invention, a plant with modified flower morphology can be obtained by suppressing the function of a transcription factor such as KAN1, YAB1 or PHB. Hence, the present invention can be used in various types of agriculture and horticulture, agribusiness, as well as the industry of processing agricultural products and the food industry. Moreover, the present invention is considered to be very useful.

What is claimed is:

1. A method for producing a dicotyledon with modified flower morphology, comprising the steps of:
   obtaining a transformed cell by introducing a chimeric DNA molecule into a dicotyledonous cell; and
   regenerating a transformed plant from said transformed cell, wherein said chimeric DNA molecule comprises is a DNA molecule encoding a transcription factor and a DNA molecule encoding a functional peptide converting said transcription factor into a transcription repressor wherein the chimeric DNA molecule is expressed which results in the plant having a modified flower petal morphology as compared to a non-transformed plant, and wherein said DNA molecule encoding said transcription factor is selected from the group consisting of:
   (a) a DNA molecule encoding the amino acid sequence of SEQ ID NO: 4;
   (b) a DNA molecule comprising the nucleotide sequence of SEQ ID NO: 3;
   (c) a DNA molecule encoding the amino acid sequence of SEQ ID NO: 4 including substitution, deletion, insertion and/or addition of 1 to 10 amino acids, and
   (d) a DNA molecule encoding an amino acid sequence having an identity of not less than 90% to the amino acid sequence of SEQ ID NO: 4,
   wherein said dicotyledon belongs to sympetalae.

2. The method according to claim 1, wherein said functional peptide is a peptide having the amino acid sequence of SEQ ID NO:22.

3. The method according to claim 1, wherein said sympetalae is a morning glory.

4. The method according to claim 1, wherein said flower morphology is petal morphology.

5. A plant produced by the method according to claim 1.

6. The method according to claim 1, wherein said functional peptide is a peptide having the amino acid sequence of any one of SEQ ID NOs: 10, 11, 12, 13, 15, 16, 20, 23, 24, 25, 27 and 28.

* * * * *

UNITED STATES PATENT AND TRADEMARK OFFICE
CERTIFICATE OF CORRECTION

PATENT NO. : 8,314,291 B2  
APPLICATION NO. : 12/672489  
DATED : November 20, 2012  
INVENTOR(S) : Ono et al.

Page 1 of 1

It is certified that error appears in the above-identified patent and that said Letters Patent is hereby corrected as shown below:

In the Specifications

In column 2 at line 30, Change "NIB)" to --PHB)--.

In column 4 at line 52, Change "ATYAB1 SRDX" to --ATYAB1SRDX--.

In column 7 at line 50, Change "motif" to --motif,--.

In column 14 at line 11-12 (approx.), Change "pBluscript." to --pBluescript.--.

In column 14 at line 15, Change "fragment" to --fragment,--.

In column 17 at line 9, Change "transformant" to --transformant.--.

In column 17 at line 27, Change "ATYAB1 SRDX" to --ATYAB1SRDX--.

In the Claims

In column 55 at line 52 (approx.), Claim 1, after "comprises" delete the word "is".

Signed and Sealed this  
Ninth Day of July, 2013

Teresa Stanek Rea  
*Acting Director of the United States Patent and Trademark Office*